(12) United States Patent
Oh et al.

(10) Patent No.: US 11,230,570 B2
(45) Date of Patent: Jan. 25, 2022

(54) PEPTIDE FOR REGULATING REACTIVITY TO SEROTONIN REUPTAKE INHIBITOR BASED ANTIDEPRESSANT, AND USE THEREOF

(71) Applicant: DAEGU GYEONGBUK INSTITUTE OF SCIENCE AND TECHNOLOGY, Daegu (KR)

(72) Inventors: Yong Seok Oh, Daegu (KR); Seo Jin Oh, Busan (KR); Jin Hyuk Jang, Gyeongsangnam-do (KR); Jeong Rak Park, Gyeonggi-do (KR); Chang Hun Shin, Daegu (KR); Min Seok Jeong, Chungcheongbuk-do (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 0 days.

(21) Appl. No.: 17/261,249

(22) PCT Filed: Jul. 26, 2019

(86) PCT No.: PCT/KR2019/009318
§ 371 (c)(1),
(2) Date: Jan. 19, 2021

(87) PCT Pub. No.: WO2020/022828
PCT Pub. Date: Jan. 30, 2020

(65) Prior Publication Data
US 2021/0269481 A1    Sep. 2, 2021

(30) Foreign Application Priority Data
Jul. 26, 2018  (KR) .................. 10-2018-0087304

(51) Int. Cl.
*C07K 7/08* (2006.01)
*A61P 25/24* (2006.01)
(Continued)

(52) U.S. Cl.
CPC .............. *C07K 7/08* (2013.01); *A61K 31/137* (2013.01); *A61K 38/10* (2013.01); *A61K 38/16* (2013.01); *A61P 25/24* (2018.01); *C07K 14/00* (2013.01)

(58) Field of Classification Search
CPC ........ C07K 7/08; C07K 14/00; A61K 31/137; A61K 38/10; A61K 38/16; A61P 25/24
See application file for complete search history.

(56) References Cited

U.S. PATENT DOCUMENTS

2005/0182002 A1    8/2005   Gordon et al.
2014/0107104 A1    4/2014   Nishi et al.

FOREIGN PATENT DOCUMENTS

| KR | 10-2009-0117286 A | 11/2009 |
| KR | 10-2013-0009104 A | 1/2013 |
| KR | 10-2018-0024527 A | 3/2018 |

OTHER PUBLICATIONS

Ozorowski, Structure of a C-terminal AHNAK peptide in a 1:2:2 complex with S100A10 and an acetylated N-terminal peptide of annexin A2, Acta Cryst, D69, 92-104 (Year: 2013).*

(Continued)

*Primary Examiner* — Kevin S Orwig
*Assistant Examiner* — John Michael Cronin
(74) *Attorney, Agent, or Firm* — Harness, Dickey & Pierce, P.L.C.

(57) ABSTRACT

Provided are: a peptide for regulating reactivity to a serotonin reuptake inhibitor-based antidepressant; a vector and a pharmaceutical composition for preventing or treating depression, which comprise same; a method for screening (Continued)

for an antidepressant by evaluating the activity of mossy cells; and the like.

18 Claims, 11 Drawing Sheets

Specification includes a Sequence Listing.

(51) Int. Cl.
   *A61K 31/137* (2006.01)
   *A61K 38/10* (2006.01)
   *A61K 38/16* (2006.01)
   *C07K 14/00* (2006.01)

(56) References Cited

OTHER PUBLICATIONS

Oh, Y-S, et al.; "SMARCA3, a Chromatin-Remodeling Factor, Is Required for p11-Dependent Antidepressant Action", Cell 152, 831-843, 2013.

Svenningsson, P., et al.; "p11 and its role in depression and therapeutic responses to antidepressants", Nat Rev Neurosci. Oct. 2013; 14(10): 673-680.

Seo, J-S, et al.; "Elevation of p11 in lateral habenula mediates depression-like behavior", Molecular Psychiatry (2018) 23, 1113-1119.

Bharadwaj, A., et al.; "Annexin A2 Heterotetramer: Structure and Function", Int. J. Mol. Sci. 2013, 14, 6259-6305.

Choi, K-S, et al.; "p11 Regulates extracellular plasmin production and invasiveness of HT1080 fibrosarcoma cells", The FASEB Journal, vol. 17, Feb. 2003, pp. 235-246.

Kwon, M., et al.; "S100A10, Annexin A2, and Annexin A2 Heterotetramer as Candidateplasminogen Receptors", Frontiers in Bioscience 10, 300-325, Jan. 1, 2005.

Laumonnier, Y., et al.; "Identification of the annexinA2 heterotetramer as a receptor for the plasmin-induced signaling in human peripheral monocytes", Blood, vol. 107, No. 8, Apr. 15, 2006, pp. 3342-3349.

Kosugi, S., et al.; "Six Classes of Nuclear Localization Signals Specific to Different Binding Grooves of Importin a*", The Journal of Biological Chemistry vol. 284, No. 1, pp. 478-485, Jan. 2, 2009.

Liu, Y, et al.; "Annexin A2 complexes with S100 proteins: structure, function and pharmacological manipulation", British Journal of Pharmacology (2015) 172 1664-1676.

Oh, S-J, et al.; "Hippocampal mossy cell involvement in behavioral and neurogenic responses to chronic antidepressant treatment", Molecular Psychiatry, 2019, pp. 1-14.

International Search Report from corresponding PCT Application No. PCT/KR2019/009318, dated Oct. 29, 2019.

* cited by examiner

SEQUENCE LISTING

<160> NUMBER OF SEQ ID NOS: 11

<210> SEQ ID NO 1
<211> LENGTH: 20
<212> TYPE: PRT
<213> ORGANISM: Artificial Sequence
<220> FEATURE:
<223> OTHER INFORMATION: PASIP

<400> SEQUENCE: 1

Gly Asn Gly Asn Gly Lys Val Thr Phe Pro Lys Met Lys Ile Pro Lys
1               5                   10                  15

Phe Ser Gly Arg
            20

<210> SEQ ID NO 2
<211> LENGTH: 23
<212> TYPE: PRT

```
<213> ORGANISM: Artificial Sequence
<220> FEATURE:
<223> OTHER INFORMATION: C3xNLS

<400> SEQUENCE: 2

Pro Lys Lys Lys Arg Lys Val Asp Pro Lys Lys Lys Arg Lys Val Asp
1               5                   10                  15

Pro Lys Lys Lys Arg Lys Val
            20

<210> SEQ ID NO 3
<211> LENGTH: 18
<212> TYPE: PRT
<213> ORGANISM: Artificial Sequence
<220> FEATURE:
<223> OTHER INFORMATION: AHNAK1

<400> SEQUENCE: 3

Gly Lys Val Thr Phe Pro Lys Met Lys Ile Pro Lys Phe Thr Phe Ser
1               5                   10                  15

Gly Arg

<210> SEQ ID NO 4
<211> LENGTH: 249
<212> TYPE: PRT
<213> ORGANISM: Artificial Sequence
<220> FEATURE:
<223> OTHER INFORMATION: AcGFP1-myc control

<400> SEQUENCE: 4

Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
        115                 120                 125

Thr Asp Phe Lys Glu Asp Gly Asn Ile Leu Gly Asn Lys Met Glu Tyr
    130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Ile Tyr Phe Gly Phe
    210                 215                 220
```

```
Val Thr Ala Ala Ala Ile Thr His Gly Met Asp Glu Leu Tyr Lys Glu
225                 230                 235                 240

Gln Lys Leu Ile Ser Glu Glu Asp Leu
            245
```

<210> SEQ ID NO 5
<211> LENGTH: 279
<212> TYPE: PRT
<213> ORGANISM: Artificial Sequence
<220> FEATURE:
<223> OTHER INFORMATION: AcGFP1-myc C-AHNAK1

<400> SEQUENCE: 5

```
Met Val Ser Lys Gly Ala Glu Leu Phe Thr Gly Ile Val Pro Ile Leu
1               5                   10                  15

Ile Glu Leu Asn Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Ser Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Ile Gln Glu
                85                  90                  95

Arg Thr Ile Phe Phe Glu Asp Asp Gly Asn Tyr Lys Ser Arg Ala Glu
            100                 105                 110

Val Lys Phe Glu Gly Asp Thr Leu Val Asn Arg Ile Glu Leu Thr Gly
        115                 120                 125

Thr Asp Phe Lys Glu Asp Gly Asn Ile Leu Gly Asn Lys Met Glu Tyr
130                 135                 140

Asn Tyr Asn Ala His Asn Val Tyr Ile Met Thr Asp Lys Ala Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Ile Tyr Phe Gly Phe
210                 215                 220

Val Thr Ala Ala Ala Ile Thr His Gly Met Asp Glu Leu Tyr Lys Glu
225                 230                 235                 240

Gln Lys Leu Ile Ser Glu Glu Asp Leu Gly Asn Gly Asn Gly Asn Gly
                245                 250                 255

Asn Gly Asn Gly Ser Gly Lys Val Thr Phe Pro Lys Met Lys Ile Pro
            260                 265                 270

Lys Phe Thr Phe Ser Gly Arg
        275
```

<210> SEQ ID NO 6
<211> LENGTH: 296
<212> TYPE: PRT
<213> ORGANISM: Artificial Sequence
<220> FEATURE:
<223> OTHER INFORMATION: N-AHNAK1-AcGFP1-myc C3xNLS

<400> SEQUENCE: 6

```
Gly Lys Val Thr Phe Pro Lys Met Lys Ile Pro Lys Phe Thr Phe Ser
1               5                   10                  15

Gly Arg Glu Gln Lys Leu Ile Ser Glu Glu Asp Leu Ser Lys Gly Ala
            20                  25                  30

Glu Leu Phe Thr Gly Ile Val Pro Ile Leu Ile Glu Leu Asn Gly Asp
        35                  40                  45

Val Asn Gly His Lys Phe Ser Val Ser Gly Glu Gly Glu Gly Asp Ala
50                  55                  60

Thr Tyr Gly Lys Leu Thr Leu Lys Phe Ile Cys Thr Thr Gly Lys Leu
65                  70                  75                  80

Pro Val Pro Trp Pro Thr Leu Val Thr Thr Leu Ser Tyr Gly Val Gln
                85                  90                  95

Cys Phe Ser Arg Tyr Pro Asp His Met Lys Gln His Asp Phe Phe Lys
            100                 105                 110

Ser Ala Met Pro Glu Gly Tyr Ile Gln Glu Arg Thr Ile Phe Phe Glu
        115                 120                 125

Asp Asp Gly Asn Tyr Lys Ser Arg Ala Glu Val Lys Phe Glu Gly Asp
    130                 135                 140

Thr Leu Val Asn Arg Ile Glu Leu Thr Gly Thr Asp Phe Lys Glu Asp
145                 150                 155                 160

Gly Asn Ile Leu Gly Asn Lys Met Glu Tyr Asn Tyr Asn Ala His Asn
                165                 170                 175

Val Tyr Ile Met Thr Asp Lys Ala Lys Asn Gly Ile Lys Val Asn Phe
            180                 185                 190

Lys Ile Arg His Asn Ile Glu Asp Gly Ser Val Gln Leu Ala Asp His
        195                 200                 205

Tyr Gln Gln Asn Thr Pro Ile Gly Asp Gly Pro Val Leu Leu Pro Asp
    210                 215                 220

Asn His Tyr Leu Ser Thr Gln Ser Ala Leu Ser Lys Asp Pro Asn Glu
225                 230                 235                 240

Lys Arg Asp His Met Ile Tyr Phe Gly Phe Val Thr Ala Ala Ala Ile
                245                 250                 255

Thr His Gly Met Asp Glu Leu Tyr Lys Ser Gly Leu Arg Ser Arg Ala
            260                 265                 270

Asp Pro Lys Lys Lys Arg Lys Val Asp Pro Lys Lys Lys Arg Lys Val
        275                 280                 285

Asp Pro Lys Lys Lys Arg Lys Val
    290                 295

<210> SEQ ID NO 7
<211> LENGTH: 69
<212> TYPE: DNA
<213> ORGANISM: Artificial Sequence
<220> FEATURE:
<223> OTHER INFORMATION: C3xNLS

<400> SEQUENCE: 7
ccaaaaaaga agagaaaggt agatccaaaa agaagagaa aggtagatcc aaaaaagaag    60
agaaaggta                                                          69

<210> SEQ ID NO 8
<211> LENGTH: 54
<212> TYPE: DNA
<213> ORGANISM: Artificial Sequence
<220> FEATURE:
<223> OTHER INFORMATION: AHNAK1
```

<400> SEQUENCE: 8

```
ggaaaagtaa cattccctaa aatgaagatc cccaaattta ccttctctgg ccgt           54
```

<210> SEQ ID NO 9
<211> LENGTH: 768
<212> TYPE: DNA
<213> ORGANISM: Artificial Sequence
<220> FEATURE:
<223> OTHER INFORMATION: AcGFP1-myc control

<400> SEQUENCE: 9

```
gctagccacc atggtgagca agggcgccga gctgttcacc ggcatcgtgc ccatcctgat     60
cgagctgaat ggcgatgtga atggccacaa gttcagcgtg agcggcgagg gcgagggcga   120
tgccacctac ggcaagctga ccctgaagtt catctgcacc accggcaagc tgcctgtgcc   180
ctggcccacc ctggtgacca ccctgagcta cggcgtgcag tgcttctcac gctaccccga   240
tcacatgaag cagcacgact tcttcaagag cgccatgcct gagggctaca tccaggagcg   300
caccatcttc ttcgaggatg acggcaacta caagtcgcgc gccgaggtga agttcgaggg   360
cgatacccctg gtgaatcgca tcgagctgac cggcaccgat ttcaaggagg atggcaacat  420
cctgggcaat aagatggagt acaactacaa cgcccacaat gtgtacatca tgaccgacaa   480
ggccaagaat ggcatcaagg tgaacttcaa gatccgccac aacatcgagg atggcagcgt   540
gcagctggcc gaccactacc agcagaatac ccccatcggc gatggccctg tgctgctgcc   600
cgataaccac tacctgtcca cccagagcgc cctgtccaag gaccccaacg agaagcgcga   660
tcacatgatc tacttcggct tcgtgaccgc cgccgccatc acccacggca tggatgagct   720
gtacaaggag cagaaactca tctctgaaga ggatctgtga ggcgcgcc                 768
```

<210> SEQ ID NO 10
<211> LENGTH: 857
<212> TYPE: DNA
<213> ORGANISM: Artificial Sequence
<220> FEATURE:
<223> OTHER INFORMATION: AcGFP1-myc C-AHNAK1

<400> SEQUENCE: 10

```
gctagccacc atggtgagca agggcgccga gctgttcacc ggcatcgtgc ccatcctgat     60
cgagctgaat ggcgatgtga atggccacaa gttcagcgtg agcggcgagg gcgagggcga   120
tgccacctac ggcaagctga ccctgaagtt catctgcacc accggcaagc tgcctgtgcc   180
ctggcccacc ctggtgacca ccctgagcta cggcgtgcag tgcttctcac gctaccccga   240
tcacatgaag cagcacgact tcttcaagag cgccatgcct gagggctaca tccaggagcg   300
caccatcttc ttcgaggatg acggcaacta caagtcgcgc gccgaggtga agttcgaggg   360
cgatacccctg gtgaatcgca tcgagctgac cggcaccgat ttcaaggagg atggcaacat  420
cctgggcaat aagatggagt acaactacaa cgcccacaat gtgtacatca tgaccgacaa   480
ggccaagaat ggcatcaagg tgaacttcaa gatccgccac aacatcgagg atggcagcgt   540
gcagctggcc gaccactacc agcagaatac ccccatcggc gatggccctg tgctgctgcc   600
cgataaccac tacctgtcca cccagagcgc cctgtccaag gaccccaacg agaagcgcga   660
tcacatgatc tacttcggct tcgtgaccgc cgccgccatc acccacggca tggatgagct   720
gtacaaggag cagaaactca tctctgaaga ggatctgggt aacggaaatg caacgggaa    780
tggtaacgga tctggaaaag taacattccc taaaatgaag atccccaaat ttaccttctc   840
```

```
<210> SEQ ID NO 11
<211> LENGTH: 951
<212> TYPE: DNA
<213> ORGANISM: Artificial Sequence
<220> FEATURE:
<223> OTHER INFORMATION: N-AHNAK1-AcGFP1-myc C3xNLS

<400> SEQUENCE: 11
gctagccacc atggtgggat ctggaaaagt aacattccct aaaatgaaga tccccaaatt      60
taccttctct ggccgtggta acggaaatgg caacgggaat ggtaacgagc agaaactcat     120
ctctgaagag gatctgagca agggcgccga gctgttcacc ggcatcgtgc ccatcctgat     180
cgagctgaat ggcgatgtga atggccacaa gttcagcgtg agcggcgagg gcgagggcga     240
tgccacctac ggcaagctga ccctgaagtt catctgcacc accggcaagc tgcctgtgcc     300
ctggcccacc ctggtgacca ccctgagcta cggcgtgcag tgcttctcac gctacccga     360 tcacatgaag cagcacgact tcttcaagag cgccatgcct gagggctaca tccaggagcg     420
caccatcttc ttcgaggatg acggcaacta caagtcgcgc gccgaggtga agttcgaggg     480 cgatacectg gtgaatcgca tcgagctgac cggcaccgat ttcaaggagg atggcaacat     540
cctgggcaat aagatggagt acaactacaa cgcccacaat gtgtacatca tgaccgacaa     600
ggccaagaat ggcatcaagg tgaacttcaa gatccgccac aacatcgagg atggcagcgt     660
gcagctggcc gaccactacc agcagaatac ccccatcggc gatggccctg tgctgctgcc     720
cgataaccac tacctgtcca cccagagcgc cctgtccaag gacccaacg agaagcgcga     780 tcacatgatc tacttcggct tcgtgaccgc cgccgccatc acccacggca tggatgagct     840
gtacaagtcc ggactcagat ctcgagctga tccaaaaaag aagagaaagg tagatccaaa     900
aaagaagaga aaggtagatc caaaaaagaa gagaaaggta tgaggcgcgc c             951
```

PEPTIDE FOR REGULATING REACTIVITY TO SEROTONIN REUPTAKE INHIBITOR BASED ANTIDEPRESSANT, AND USE THEREOF

CROSS-REFERENCE TO RELATED APPLICATIONS

This application is a national phase application of PCT Application No. PCT/KR2019/009318 filed on Jul. 26, 2019, which claims priority to Korean Patent Application No. 10-2018-0087304 filed on Jul. 26, 2018. The entire disclosures of the applications identified in this paragraph are incorporated herein by reference.

FIELD

The present invention relates to a peptide for controlling reactivity to a serotonin reuptake inhibitor-based antidepressant and a use thereof.

BACKGROUND

Depression is an emotional pathological phenomenon that occurs regardless of objective situations, and a mood disorder that fills a patient's entire life with a depressive feeling, causes loss of interest and anhedonia, decreased psychomotor activity, pessimism, and despair. It also causes loss of appetite, insomnia, constipation, loss of sexual desire, increased susceptibility to a disease caused by decreased immune functions, and other various physical symptoms. In the art, it seems that the most promising hypothesis is that depression is caused by a lack of monoamine-based neurotransmitters such as serotonin, norepinephrine and dopamine in a synapse of the central nervous system.

Accordingly, most antidepressants have a pharmacological action of increasing the concentration of a neurotransmitter in a serotonergic or noradrenaline synapse. More specifically, as the antidepressants, according to a mechanism that increases the concentration of a neurotransmitter, generally, a tricyclic antidepressant (TCA), a monoamine oxidase inhibitor (MAOI), and a selective serotonin reuptake inhibitor (SSRI) are used. Due to a serious side effect of causing heart disease, MAOI, such as phenelzine, have not been used well these days, and tricyclic antidepressants, such as imipramine, also have considerable problems of anticholinergic side effects and sedation, and side effects on the cardiovascular system. Accordingly, recently, for antidepressants having fewer of the above side effects, the focus was on the development of an antidepressant using a selective serotonin (5-HT) reuptake inhibitor, and representatively, fluoxetine (trade name; Prozac), paroxetine (trade name; Seroxat), and sertraline (trade name; Zoloft) were developed and their efficacies have been widely recognized clinically.

However, these serotonin reuptake inhibitor-based drugs are only effective in approximately 60% patients in the total administered group, and the remaining approximately 30 to 40% patients do not show any therapeutic efficacy, and due to the broad influence of serotonergic synapses that are spread throughout the central nervous system, there is a problem of unnecessary side effects according to the drug-administered patient. In addition, it takes only one hour to increase a serotonin level in a cerebral synapse in a serotonergic drug reaction, but there is a limit in that at least three weeks of long-term medication is required to exhibit therapeutic efficacy leading to actual mood elevation in patients.

Against such a technical background, research on the mechanism of depression and the action mechanism of a therapeutic agent for depression, such as an antidepressant, and the development of a novel antidepressant based thereon are required (Korean Unexamined Patent Application No. 10-2018-0024527), but are still insufficient.

SUMMARY

Technical Problem

The present invention is directed to providing a peptide for controlling reactivity to a serotonin reuptake inhibitor-based antidepressant.

The present invention is also directed to providing a vector, which includes the peptide.

The present invention is also directed to providing a pharmaceutical composition for preventing or treating depression, which includes the peptide.

The present invention is also directed to providing a pharmaceutical composition for preventing or treating cancer, which includes the peptide.

The present invention is also directed to providing a pharmaceutical composition for preventing or treating a bleeding disorder, which includes the peptide.

The present invention is also directed to providing a pharmaceutical composition for preventing or treating a vascular inflammatory disease, which includes the peptide.

The present invention is also directed to providing a method of screening an antidepressant, which includes: measuring a neuronal activity level of mossy cells in contact with a test material; and comparing the measured neuronal activity level of the mossy cells with a neuronal activity level of the control group which is not in contact with the test material.

Technical Solution

One aspect of the present invention provides a peptide for controlling reactivity to a serotonin reuptake inhibitor-based antidepressant, which consists of an amino acid sequence of SEQ ID NO: 1.

The term "serotonin reuptake inhibitor-based antidepressant" used herein refers to a drug used to treat depression, an anxiety disorder or a personality disorder, and a material that prevents reuptake of serotonin into presynaptic cells, thereby increasing the level of serotonin capable of binding to a synaptic receptor after the serotonin level increases at the extracellular level. For example, the antidepressant may be fluoxetine, citalopram, dapoxetine, escitalopram, fluvoxamine, paroxetine, sertraline, or a combination thereof.

The term "reactivity to a serotonin reuptake inhibitor-based antidepressant" used herein refers to an in vivo physiological or pathological change of a subject to which the serotonin reuptake inhibitor-based antidepressant is administered, and more specifically, a pathological change associated with depression symptoms, for example, neurogenic or behavioral reactivity associated with depression symptoms. Here, the subject refers to a subject in need of treatment of a disease, and more specifically, may be a mammal such as a human or a non-human primate, a mouse, a rat, a dog, a cat, a horse, or a cow.

According to one embodiment, the peptide consisting of the amino acid sequence of SEQ ID NO: 1 may control reactivity to a serotonin reuptake inhibitor-based antidepressant by blocking functional assembly of a p11/AnxA2/SMARCA3 heterohexamer (or p11/AnxA2/SMARCA3 complex) produced in hippocampal mossy cells, specifically, inhibiting binding between a p11/AnxA2 complex and SMARCA3. That is, the peptide may inhibit the activity of p11 or a p11-related complex to affect a physiological change according to the administration of a serotonin reuptake inhibitor-based antidepressant.

In one embodiment, the peptide may consist of an amino acid sequence having 75% or more, preferably 80% or more, more preferably 90% or more, and most preferably 95% or more homology with the amino acid sequence of SEQ ID NO: 1. Here, the "homology" refers to a percentage of identity between two polynucleotides or polypeptide moieties. The homology between sequences from one moiety to another moiety may be determined by techniques in the known art. For example, homology may be determined by directly aligning sequence information between two polynucleotide molecules or two polypeptide molecules, for example, parameters such as a score, identity and similarity, using a computer program which can align sequence information and is easily available (e.g., BLAST 2.0).

The peptide may further include a target sequence, a tag, a labeled residue, and an amino acid sequence prepared for a specific purpose of increasing half-life or stability. In addition, to obtain higher chemical stability, reinforced pharmacological characteristics (half-life, uptake, titer, efficacy, etc.), changed specificity (e.g., a broad biological activity spectrum) and reduced antigenicity, a protecting group may be attached to the N- or C-terminus of the peptide. Preferably, the protecting group may be an acetyl group, a fluorenyl methoxy carbonyl group, a formyl group, a palmitoyl group, a myristyl group, a stearyl group or polyethylene glycol (PEG), but may be any component that can improve the stability of the peptide without limitation.

In addition, to improve transfer of the peptide into the nucleus of mossy cells, the peptide may further include a nuclear localization sequence (NLS), for example, an amino acid sequence of SEQ ID NO: 2. Since the p11/AnxA2/SMARCA3 complex is formed in the nucleus of mossy cells, the addition of the sequence may contribute to control of a subject's reactivity to a serotonin reuptake inhibitor-based antidepressant.

The peptide may be obtained by various methods widely known in the art. As an example, the peptide may be prepared using a polynucleotide recombination and protein expression system, an in vitro synthesis method through chemical synthesis such as peptide synthesis, and a cell-free protein synthesis method.

Another aspect of the present invention provides a vector, which includes the peptide consisting of the amino acid sequence of SEQ ID NO: 1.

In the following description of the vector, the "peptide," "serotonin reuptake inhibitor-based antidepressant" and "reactivity control" are as described above.

In one embodiment, the peptide may be provided to a subject in the form that nucleotides encoding the peptide are included in a vector, and here, tissue- and cell-specific promoters may be located upstream of the nucleotides encoding the peptide, thereby inducing tissue- and cell-specific expression. For example, the peptide may be specifically activated or expressed in hippocampal mossy cells using a mossy cell-specific promoter, and therefore, the reactivity of a subject to the serotonin reuptake inhibitor-based antidepressant may be controlled.

The term "promoter" used herein refers to an untranslated base sequence present upstream of a coding region, which includes a binding site for a polymerase and has an ability of initiating transcription into mRNA of a gene downstream of the promoter, that is, a DNA region to which a polymerase binds such that gene transcription is initiated. The promoter may be present at the 5' end of an mRNA transcription initiation site. In addition, the promoter may be a constitutive promoter or inducible promoter.

The term "vector" used herein refers to a DNA construct containing a DNA sequence operably linked to a suitable regulatory sequence that can express DNA in a suitable host. The vector may be a plasmid, a phage particle or simply a potential genomic insert. When transformed into a suitable host, the vector may be replicated and function regardless of a host genome, or in some cases, integrated into the genome itself. For example, the vector may include a plasmid, an adenovirus, an adeno-related virus, a retrovirus, a lentivirus, a herpes simplex virus, or a vaccinia virus.

Still another aspect of the present invention provides a pharmaceutical composition for preventing or treating depression, which includes the peptide consisting of the amino acid sequence of SEQ ID NO: 1.

In the following description of the pharmaceutical composition for preventing or treating depression, the "peptide" and "reactivity control" are as described above.

The term "prevention" used herein refers to all actions of inhibiting the symptoms of depression or delaying the occurrence of depression by administration of the pharmaceutical composition according to one embodiment.

The term "treatment" used herein refers to all actions involved in alleviating or beneficially changing symptoms of depression by administration of the pharmaceutical composition according to one embodiment.

According to one embodiment, the peptide consisting of the amino acid sequence of SEQ ID NO: 1 is located at a hydrophobic binding pocket produced on the surface of a p11/AnxA2 heterotetramer. Therefore, in a reaction with the p11/AnxA2 heterotetramer, the peptide has a competitive relationship with endogenous SMARCA3, and in other words, may inhibit activity of p11 or a p11 complex by preventing the functional assembly of a p11/AnxA2/SMARCA3 heterohexamer (or p11/AnxA2/SMARCA3 complex).

Meanwhile, changes in activity of the p11 and the p11 complex (p11/AnxA2/SMARCA3) have different characteristics depending on a neural region and neural cells in which these molecules are expressed and produced. For example, in the hippocampus, nucleus accumbens and cerebral cortex regions, level(s) of the p11 and/or p11/AnxA2/SMARCA3 complex in a depression animal model are reduced, whereas in a lateral habenula region, rather, the expression/activity levels of p11 and a related complex increase due to the induction of stress and depression (Elevation of p11 in lateral habenula mediates depression-like behavior. Molecular psychiatry. 23, 1113-1119 (2018)). Therefore, the composition may be applied to treat depression through site-specific delivery into nervous tissue (e.g., delivery to the lateral habenula region).

In addition, a conventional serotonin reuptake inhibitor-based antidepressant carries unnecessary side effects depending on a patient to which the above-mentioned drug is administered due to the widespread influence of serotonergic synapses throughout the central nervous system. Against such a technical background, the composition may control the therapeutic efficacy of the serotonin reuptake inhibitor-based antidepressant, and for example, reduce side effects according to chronic or long-term administration to a region, other than mossy cells. In this case, the composition may be used as a pharmaceutical composition for treating depression, which is used in combination with a serotonin reuptake inhibitor-based antidepressant.

In one embodiment, the pharmaceutical composition may include a pharmaceutically acceptable carrier such as a colloidal suspension, powder, saline, lipids, liposomes, microspheres, or nano spherical particles. These may form a complex with a carrier or may be associated therewith, and may deliver or transfer an active ingredient into a living body using a delivery system known in the art, for example, lipids, liposomes, microparticles, gold, nanoparticles, a polymer, a condensing agent, polysaccharides, poly(amino acid)s, dendrimers, saponins, an adsorption enhancing substance or fatty acids. For example, by being included in a viral or non-viral vector, the peptide may be transported or delivered into a living body.

Moreover, as a pharmaceutically acceptable carrier, the pharmaceutical composition may include lactose, dextrose, sucrose, sorbitol, mannitol, starch, acacia gum, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, and mineral oil, which is conventionally used in formulation, and further include a lubricant, a wetting agent, a sweetening agent, a flavoring agent, an emulsifier, a suspending agent or a preservative, other than the above-mentioned components.

The pharmaceutical composition may be administered orally or parenterally (e.g., intramuscularly, intravenously, intraperitoneally, subcutaneously, intradermally or locally) depending on a desired method, a dose of the pharmaceutical composition may vary depending on the condition and body weight of a patient, the severity of a disease, a drug type, an administration route and time, and may be suitably selected by one of ordinary skill in the art. The pharmaceutical composition is administered at a pharmaceutically effective amount. Here, the "pharmaceutically effective amount" refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The pharmaceutical composition of the present invention may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by one of ordinary skill in the art.

Specifically, the effective amount of the pharmaceutical composition of the present invention may vary depending on a patient's age, sex, condition and body weight, an absorption rate of the active ingredient in the body, an inactivation rate, an excretion rate, a disease type or a co-used drug, and may be increased or decreased depending on an administration route, the severity of obesity, a sex, a body weight or an age.

Yet another aspect of the present invention provides a pharmaceutical composition for preventing or treating cancer, which includes the peptide consisting of the amino acid sequence of SEQ ID NO: 1.

In the following description of the pharmaceutical composition for preventing or treating cancer, the "peptide," "prevention" and "treatment" are as described above.

The term "cancer" used herein is the umbrella term for diseases caused by cells with an aggressive characteristic of developing and growing despite a normal growth limit, an invasive characteristic of penetrating into surrounding tissue and a metastatic characteristic of spreading to other regions of a body. The cancer may be, for example, pancreatic cancer, kidney cancer, colorectal cancer, liver cancer, leukemia, prostate cancer, head and neck cancer, lung cancer or breast cancer.

Meanwhile, it has been reported that the expression of Annexin A2 (AnxA2) or a complex associated therewith in a lesion plays a critical role in malignant transformation or metastasis of cancer, and is highly involved in the progression of, specifically, pancreatic ductal adenocarcinoma (PDAC), renal cell carcinoma (RCC), colorectal carcinoma (RC), hepatocellular carcinoma (HCC), acute promyelocytic leukemia (APL), prostate cancer, and head and neck cancer (Annexin A2 heterotetramer: structure and function, Annexin A2 heterotetramer: structure and function. Int J Mol Sci. 2013 Mar. 19; 14(3):6259-305). In addition, it has been known that the activity of the p11 and the p11 complex (p11/AnxA2/SMARCA3) affects invasiveness of a tumor such as lung cancer or breast cancer (p11 controls extracellular plasmin production and invasiveness of HT1080 fibrosarcoma cells. FASEB J. 2003 February; 17(2):235-46). Therefore, a composition capable of inhibiting the activity of the complex may be used to treat cancer.

Yet another aspect of the present invention provides a method of treating depression, which includes administering a therapeutically effective dose of the composition including the peptide consisting of the amino acid sequence of SEQ ID NO: 1 as an active ingredient to a subject.

Yet another aspect of the present invention provides a use of the composition including the peptide consisting of the amino acid sequence of SEQ ID NO: 1 as an active ingredient to treat depression or prepare a drug for treating the same.

Yet another aspect of the present invention provides a pharmaceutical composition for preventing or treating a bleeding disorder, which includes the peptide consisting of the amino acid sequence of SEQ ID NO: 1.

In the following description of the pharmaceutical composition for preventing or treating a bleeding disorder, the "peptide," "prevention" and "treatment" are as described above.

The term "bleeding disorder" refers to quantitative or functional abnormalities occurring in one or several parts of several factors (a blood vessel, a platelet, and a blood coagulation system) involved in the hemostasis process. The bleeding disorder is the umbrella term for blood disorders which spontaneously occur due to blood discharged from tissue or blood disorders with a symptom of bleeding not stopping, which are caused by a local injury, and may include, for example, thrombotic thrombocytopenic purpura (TTP), hemolytic uremic syndrome (HUS), essential thrombocytosis, Von Willebrand Disease, Bernard-Soulier syndrome, Glanzmann's thrombasthenia, idiopathic thrombocytopenic purpura (ITP), idiopathic thrombocytopenic purpura (acute leukemia and aplastic anemia), disseminated intravascular coagulation (DIC), hemophilia, vitamin K deficiency, fibrinogenemia, allergic purpura, hereditary hemorrhagic telangiectasia, Ehlers-Danlos syndrome, scurvy, hemangioma, hemarthrosis, and thrombocytopenia.

The Annexin A2 (AnxA2)/p11 complex plays a critical role in thrombolysis, and specifically, it has been reported that, in AnxA2 or p11 knockout mice, thrombopoiesis is accelerated by lowering a fibrolysis rate in a blood vessel (S100A10, annexin A2, and annexin a2 heterotetramer as candidate plasminogen receptors. Front Biosci. 2005 Jan. 1; 10:300-25). Therefore, a composition capable of inhibiting the activity of the complex may be used to treat a bleeding disorder.

Yet another aspect of the present invention provides a method of treating a bleeding disorder, which includes administering a therapeutically effective amount of the composition including the peptide consisting of the amino acid sequence of SEQ ID NO: 1 as an active ingredient to a subject.

Yet another aspect of the present invention provides a use of the composition including the peptide consisting of the amino acid sequence of SEQ ID NO: 1 as an active ingredient to treat a bleeding disorder or prepare a drug for treating the disorder.

Yet another aspect of the present invention provides a pharmaceutical composition for preventing or treating a vascular inflammatory disease, which includes the peptide consisting of the amino acid sequence of SEQ ID NO: 1.

In the following description of the pharmaceutical composition for preventing or treating a vascular inflammatory disease, the "peptide," "prevention" and "treatment" are as described above.

The term "vascular inflammatory disease" refers to a blood vessel disease caused by inflammation. For example, the vascular inflammatory disease may include arteriosclerosis, hypertension, angina, myocardial infarction, ischemic heart disease, heart failure, complications occurring after transluminal angioplasty, cerebral infarction, cerebral hemorrhage and stroke.

It has been reported that the Annexin A2 (AnxA2)/p11 complex is closely related to an antiinflammatory response in a blood vessel, and specifically, inactivation of the complex can inhibit proinflammatory signals (Identification of the annexin A2 heterotetramer as a receptor for the plasminin-induced signaling in human peripheral monocytes. Blood. 2006 Apr. 15; 107(8):3342-9). Therefore, a composition capable of inhibiting the activity of the complex may be used to treat a vascular inflammatory disease.

Yet another aspect of the present invention provides a method of treating a vascular inflammatory disease, which includes administering a therapeutically effective amount of the composition including the peptide consisting of the amino acid sequence of SEQ ID NO: 1 as an active ingredient to a subject.

Yet another aspect of the present invention provides a use of the composition including the peptide consisting of the amino acid sequence of SEQ ID NO: 1 as an active ingredient to treat a vascular inflammatory disease or prepare a drug for treating the same.

Yet another aspect of the present invention provides a method of screening an antidepressant, which includes: measuring a neuronal activity level of mossy cells in contact with a test material; and comparing the measured neuronal activity level of the mossy cells with a neuronal activity level of the control group which is not in contact with the test material.

The term "antidepressant" used herein is a material for treating or relieving depression symptoms such as a depressive mood, decreased motivation, interest and mental activity, nervousness (anxiety), loss of appetite, insomnia, persistent sadness and anxiety, and may include a tricyclic antidepressant, MAOI, or a selective serotonin reuptake inhibitor (SSRI), and for example, all of the SSRI-based antidepressants and therapeutic adjuvants for improving the efficacy of treating depression.

According to one embodiment, it was confirmed that a change in neuronal activity of mossy cells in the dentate gyrus affects neurogenic and behavioral responses according to the administration of an antidepressant, and the neuronal activity of mossy cells is closely related to the formation of the p11/AnxA2/SMARCA3 complex. Therefore, the increased neuronal activity of mossy cells, an increased level of p11/AnxA2/SMARCA3 complex in mossy cells, or an increased binding level between the p11/AnxA2 complex and SMARCA3 in mossy cells may be used as indicators to evaluate reactive or therapeutic efficacy of an antidepressant candidate.

In one embodiment, the measurement of the neuronal activity level of the mossy cells may be performed by detection of a neuronal activity-specific marker (e.g., the number of BrdU+ proliferating cells) of mossy cells, electrophysiological analysis and a combination thereof, and for example, by measuring a spontaneous firing rate. Accordingly, when the neuronal activity level of the mossy cells in contact with the test material increases, compared to a control, the method may further include determining the test material as an antidepressant. The level change may include an 1%, 2%, 3%, 4%, 5%, 10%, 20%, 30%, 40%, 50%, 60%, 70%, 80%, 90%, 100%, 200%, 300%, 400%, 500%, 600%, 700%, 800%, 900%, or 1000% or more increase in activity level, compared to the control.

In another embodiment, the measurement of a neuronal activity level of mossy cells may be performed by measuring a level of the p11/AnxA2/SMARCA3 complex in mossy cells or a binding level between the p11/AnxA2 complex and SMARCA3 using a method widely known in the art (e.g., immunoprecipitation assay). Accordingly, the method may further include selecting a material for promoting the formation of a p11/AnxA2/SMARCA3 complex in mossy cells, compared to a control, that is, determining a material which forms a p11/AnxA2/SMARCA3 complex in the mossy cells or increases binding between a p11/AnxA2 complex and SMARCA3 as an antidepressant. The level change may include an 1%, 2%, 3%, 4%, 5%, 10%, 20%, 30%, 40%, 50%, 60%, 70%, 80%, 90%, 100%, 200%, 300%, 400%, 500%, 600%, 700%, 800%, 900% or 1000% or more increase in activity level, compared to a control.

Meanwhile, the measurement of the neuronal activity level of mossy cells may be evaluated at the cellular level, or evaluated for a depression animal model at the subject level.

In the screening method, the test material may be any one selected from the group consisting of a low molecular weight compound, an antibody, an antisense nucleotide, short interfering RNA, short hairpin RNA, a nucleic acid, a protein, a peptide, other extracts and natural substances.

The test material and hippocampal mossy cells may have a detectable marker attached thereto. The marker may be linked into a nucleotide sequence using a gene recombination technique. The measurement of a binding level may be performed by a two-hybrid method, a co-immunoprecipitation assay, a co-localization assay, a scintillation proximity assay (SPA), a UV or chemical crosslinking method, bimolecular interaction analysis (BIA), mass spectrometry (MS), nuclear magnetic resonance (NMR), fluorescence polarization assay (FPA) and an in vitro pull-down assay or a combination thereof according to a marker type or a measurement method.

Advantageous Effects

As a peptide according to one aspect is directly involved in the formation of a p11/AnxA2/SMARCA3 complex, it can effectively control the reactivity of a serotonin reuptake inhibitor-based antidepressant, and can be applied in treatment of depression through site-specific delivery in nervous tissue. In addition, the peptide can be effectively used in various diseases associated with the formation or control of the p11/AnxA2/SMARCA3 complex.

The screening method according to one aspect is based on a key action mechanism of a newly identified antidepressant, and a novel antidepressant can be found more simply and effectively by evaluating and comparing neuronal activity levels of mossy cells.

BRIEF DESCRIPTION OF THE DRAWINGS

FIG. 1A is a schematic diagram illustrating an experimental process for confirming mossy cell-specific Cre-recombination in the hippocampus of D2-Cre transgenic mice; FIG. 1B is a result of co-localization of a Cre-dependent reporter (mTomato, red) and CRT (green, filled arrows), which is a mossy cell marker; FIG. 1C is a schematic diagram illustrating a knockout process of the p11 gene in mossy cells using a D2-Cre driver line; FIG. 1D is a result of an NFS test performed on p11 knockout mice (hereinafter, in the specification, SAL refers to a saline-administered group, and FLX refers to a fluoxetine-administered group); FIG. 1E is a result of evaluating hunger levels in a control and a p11 cKO group through a home cage feeding (HCF) test; FIG. 1F is a schematic diagram illustrating a process of genetically deleting the Smarca3 gene in mossy cells using a D2-Cre driver line; FIG. 1G is a result of an NFS test performed on Smarca3 knockout mice; FIG. 1H is a result of evaluating hunger levels in a control and a Smarca3c KO group through a HCF test; FIG. 1I is a schematic diagram illustrating a process of confirming mossy cell-specific recombination in the hippocampus of MC-Cre transgenic mice; FIG. 1J is a result of co-localization of a Cre-dependent reporter (mTomato, red) and CRT (green, filled arrows), which is a mossy cell marker; FIG. 1K is a schematic diagram illustrating a process of genetically deleting the Smarca3 gene in mossy cells using an MC-Cre driver line; FIG. 1L is a result of an NFS test performed on Smarca3 knockout mice; and FIG. 1M is a result of evaluating hunger levels by a HCF test performed on the same set of animals.

FIG. 2A is a schematic diagram of p11/AnxA2/SMARCA3 complex-inhibitory peptide (PASIP)-AcGFP1 fusion protein (PASIP-AcGFP1) and a control construct (control AcGFP1); FIG. 2B is a schematic diagram illustrating a process in which PASIP-AcGFP1 blocks the functional assembly of the p11/AnxA2/SMARCA3 heterohexamer complex; FIG. 2C is a result of confirming the disruption of the p11/AnxA2/SMARCA3 complex by PASIP-AcGFP1 through an in vitro pull-down assay; FIG. 2D is a schematic diagram illustrating a process in which recombinant AAV expressing control AcGFP1 or PASIP-AcGFP1 is stereotactically injected into the dentate gyrus of MC-Cre transgenic mice; and FIG. 2E is a set of representative immunolabeling images to exhibit mossy cell-specific expression of the control AcGFP1 or PASIP-AcGFP1 construct.

FIG. 3A is a schematic diagram of a double-Flox Cre-dependent AAV vector expressing control AcGFP1 and PASIP-AcGFP1 under the control of an EF-1α promoter; FIG. 3B is a schematic diagram illustrating the process of stereotaxic injection of a Cre-dependent AAV vector expressing the control AcGFP or PASIP-AcGFP1 construct along the rostro-caudal axis of the hippocampus (Rostral: AP −2.1 mm, ML ±1.4 mm, DV −1.95 mm. Caudal: AP −3.3 mm, ML ±2.7 mm, DV −3.6 mm); FIG. 3C is a set of representative images showing longitudinal expression of the control AcGFP or PASIP-AcGFP1 according to the rostro-caudal axis of the hippocampus of MC-Cre mice; and FIG. 3D shows results of confirming mossy cell-specific expression of the control AcGFP or PASIP-AcGFP1 construct through immunostaining with GluR2/3 (mossy cell marker), PV (basket cell marker) and NPY (HIPP cell marker).

FIG. 4A is a schematic diagram illustrating an experimental process; FIG. 4B shows representative images of α-BrdU immunostaining results; FIG. 4C is a comparative quantification result for the number of BrdU-positive cells in the subgranular zone (SGZ); FIG. 4D is a result of an NFS test; FIG. 4E is a result of evaluating hunger levels through an HCF test; FIG. 4F is a result of confirming an anxiety-related behavior pattern in a light/dark box test; and FIG. 4G is a result of confirming a despair or depression-like behavior pattern in a tail hanging test.

FIG. 5A is a schematic diagram illustrating an AcGFP1-labeling process of mossy cells for electrophysiological recording; FIG. 5B is a representative fluorescence image of mossy cells labeled with AcGFP-1 in a hippocampal section in AAV-injected mice; FIGS. 5C to 5F are results of recording the electrophysiological activity of AcGFP1-labeled mossy cells in the saline- or fluoxetine-treated dentate gyrus, representative traces and minimum-maximum plots (n=9 cells/3 mice per group, scale bar: 1 sec, Student's t-test, *p<0.05) showing a spontaneous firing rate of mossy cells by chronic FLX administration (FIGS. 5C and 5D); representative traces and minimum-maximum plots (n=9 cells/3 mice per group, scale bar: 1 sec, Student's t-test, *p<0.05) showing a spontaneous firing rate of mossy cells by acute FLX administration (FIGS. 5E and 5F); FIGS. 5G and 5H are results showing reduced electrophysiological activity of mossy cells in p11 cKO mice, and representative traces and the minimum-maximum plots (n=10 cells/3 mice for a control, n=6 cells/3 mice for p11 cKO, scale bar: 200 ms, Student's t-test. *p<0.05) showing a spontaneous firing rate of mossy cells in the dentate gyrus of a control and p11 cKO mice; and FIGS. 5I and 5J show reduced electrophysiological activity of mossy cells in Smarca3 KO mice, and representative traces and the minimum-maximum plots (n=9 cells/3 mice per group, scale bar: 200 ms, Student's t-test,

*p<0.05) showing a spontaneous firing rate of mossy cells in the dentate gyrus of a control and Smarca3 cKO mice.

Figure 6:
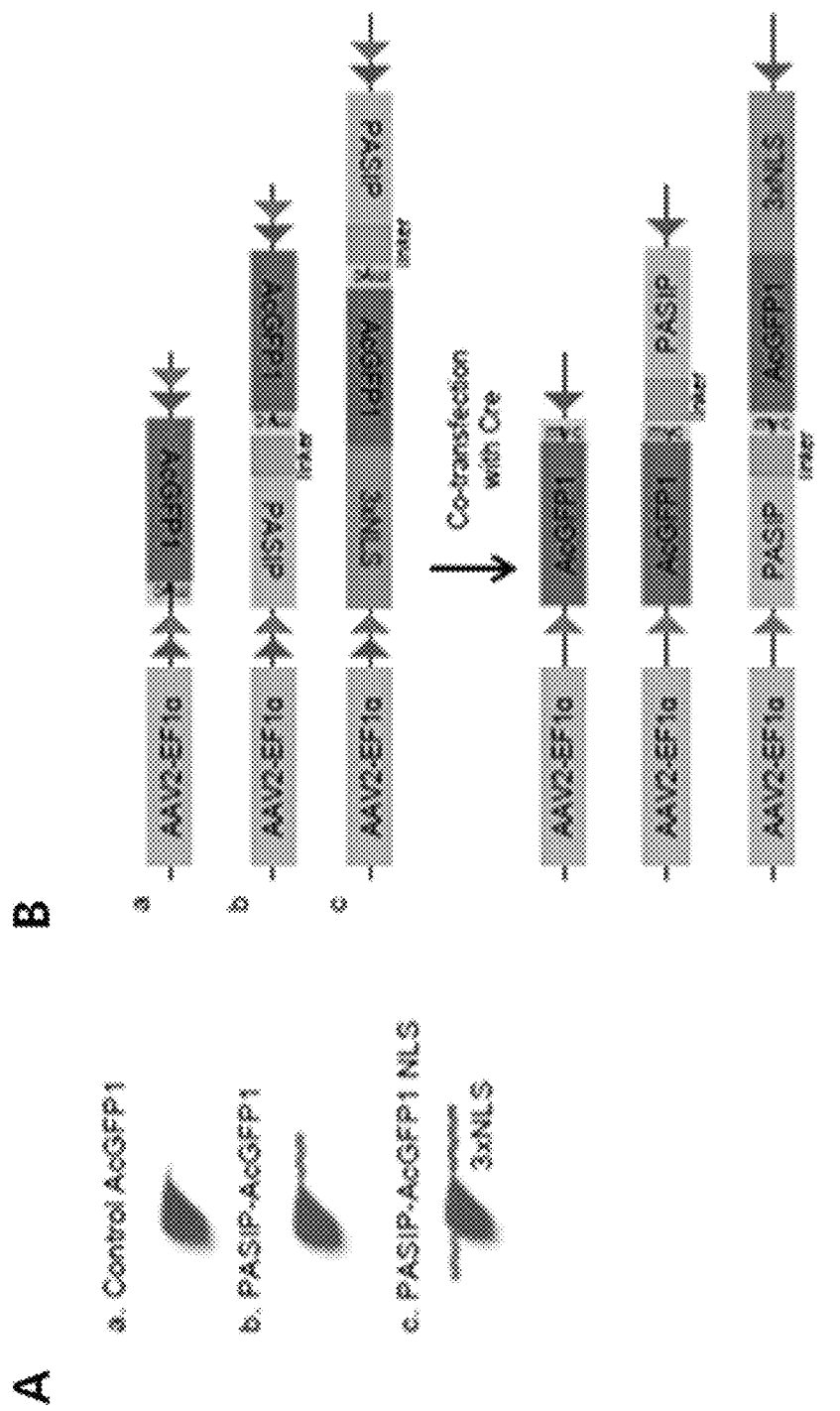

FIG. 6 shows a series of recombinant constructs inhibiting the p11/AnxA2/SMARCA3 complex:

FIG. 6A is a schematic diagram of a series of recombinant constructs, which includes control AcGFP1 (a), an inhibitory recombinant construct (b, PASIP-AcGFP) and a nucleus-targeting inhibitory recombinant construct (c, PASIP-AcGFP1-NLS); and FIG. 6B is a double-Flox AAV vector expressing control AcGFP1 (a), PASIP-AcGFP1 (b) or PASIP-AcGFP1-NLS (c) under the control of EF-1a.

Figure 7:
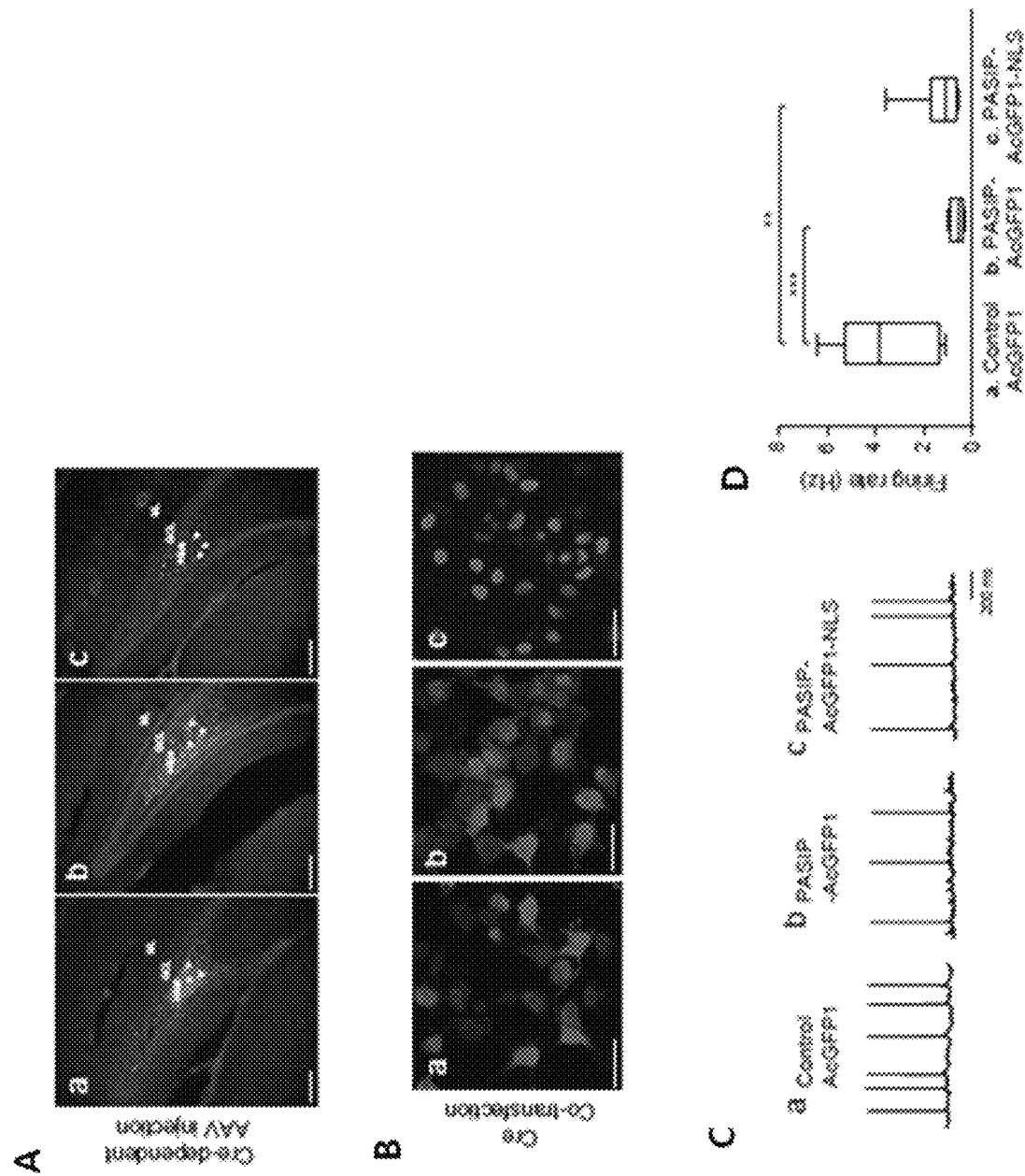

FIG. 7 shows the effect of a p11/AnxA2/SMAR complex on the firing rate (excitability) of mossy cells in the dentate gyrus:

FIG. 7A shows immunofluorescence images of mossy cell-specific expression in the dentate gyrus of the AAV-injected mice of FIG. 6; FIG. 7B shows immunofluorescence images of expression patterns of the AAV construct in HEK 293 cells; and FIGS. 7C and 7D are reduced electrophysiological activities of mossy cells in which the p11/AnxA2/SMARCA3 complex is disrupted, and representative traces and the minimum-maximum plots showing a spontaneous firing rate of mossy cells expressing each construct (n=8 cells/3 mice), scale bar: 200 ms, One-way ANOVA. $F_{(2, 25)}=12.25$, $P<0.01$, *$p<0.005$).

Figure 8:
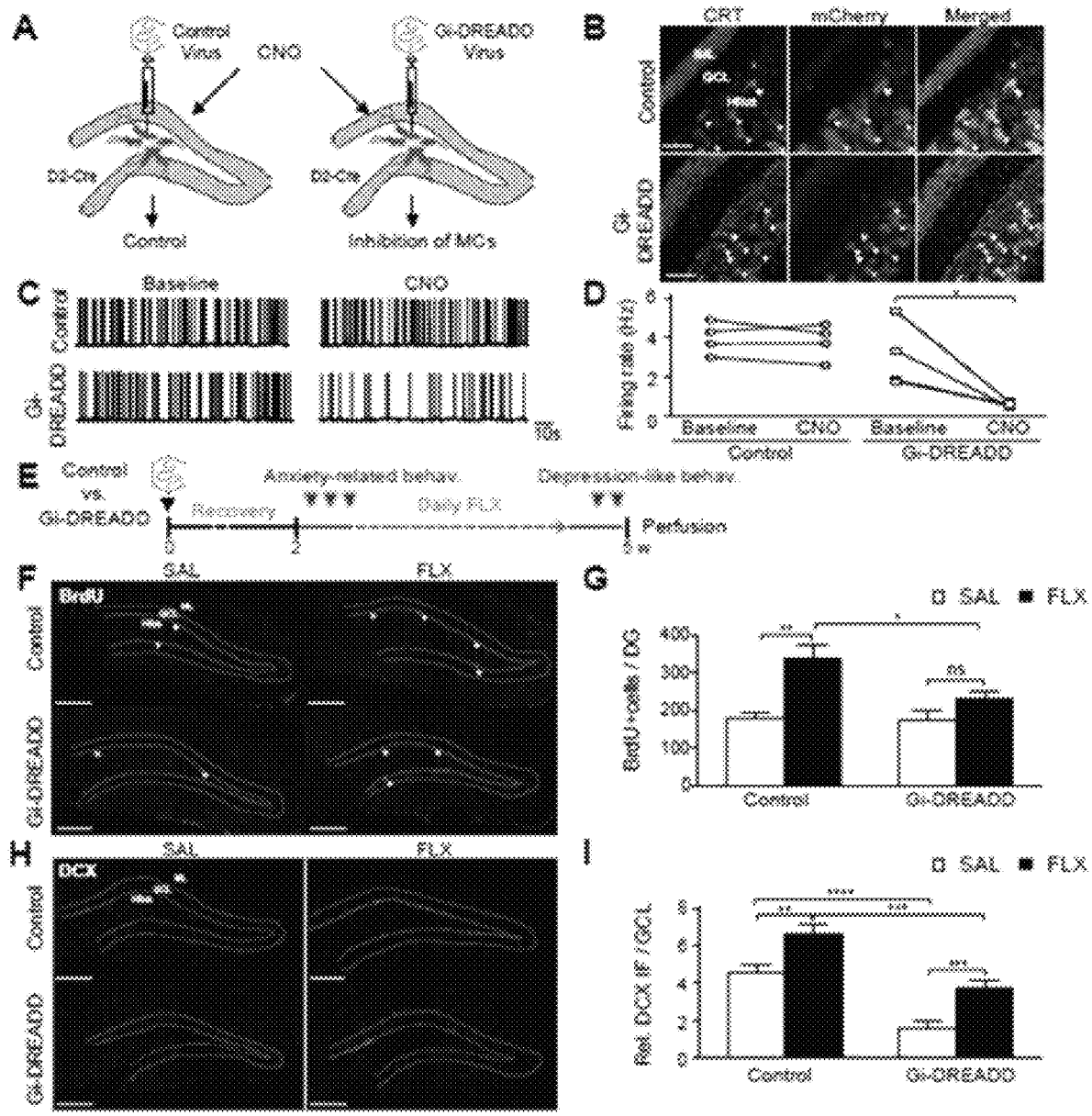

FIG. 8 shows the effect of Gi-DREADD-inhibition of mossy cells on neurogenic and behavioral responses to chronic treatment of SSRI:

FIG. 8A is a schematic diagram showing a process of silencing the activity of mossy cells using a Gi-DREADD system; FIG. 8B shows representative images showing mossy cell-specific delivery using the Gi-DREADD system; FIG. 8C shows representative traces indicating a spontaneous firing rate of mossy cells expressing control mCherry or Gi-DREADD-mCherry (Gi-DREADD) before or after the Gi-DREADD system is applied (n=4 per group. Scale bar: 200 ms, Paired student's t-test. *$p<0.05$); FIG. 8D shows representative dot plot results; FIG. 8E is a schematic diagram of an experimental process; FIG. 8F shows images visualizing proliferating neural stem cells immunostained with α-BrdU (BrdU, green); FIG. 8G is a quantification result for BrdU+ cells (filled arrows) in the subgranular zone; FIG. 8H shows results of immunostaining immature neurons after mitosis with α-doublecortin antibodies (DCX, green); and FIG. 8I is a quantitative result for relative immunofluorescent intensity (Rel. DCX IF) of DCX in subgranular and granular zones using ImageJ software.

Figure 9:
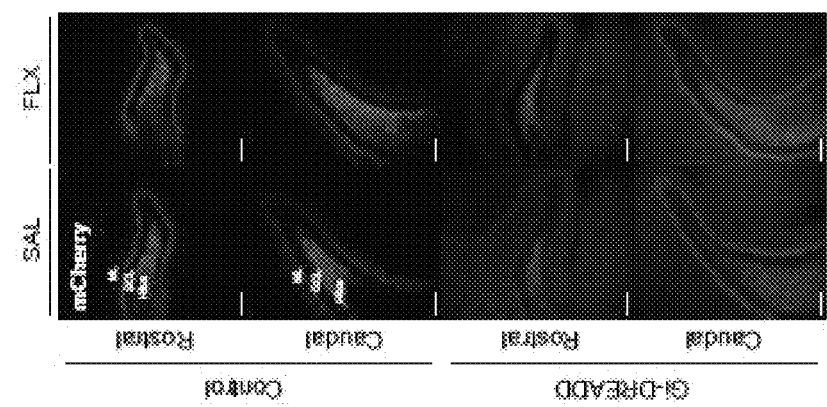
Figure 9:
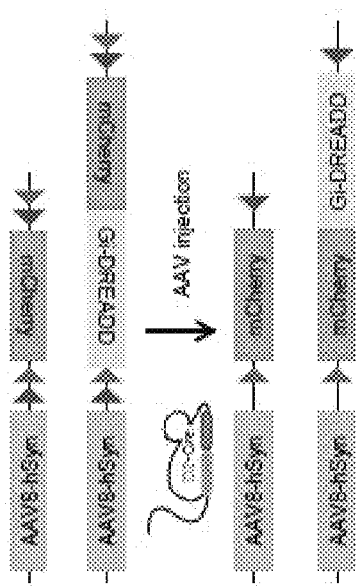
Figure 9:
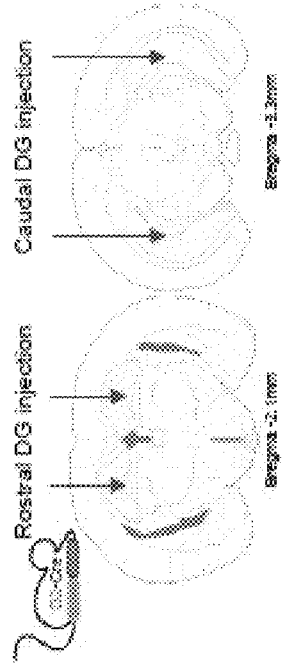

FIG. 9 shows mossy cell-specific expression of a control or Gi-DREADD construct along the rostral-caudal axis of the hippocampus:

FIG. 9A is a diagram of a double-Flox Cre-dependent AAV vector expressing the control or Gi-DREADD construct under the control of human Synapsin I (hSyn); FIG. 9B is a schematic diagram illustrating a process of stereotactically injecting Cre-dependent AAVs expressing the control or Gi-DREADD along the rostral-caudal axis of the hippocampus (Rostral: AP −2.1 mm, ML ±1.4 mm, DV −1.95 mm. Caudal: AP −3.3 mm, ML ±2.7 mm, DV −3.6 mm); and FIG. 9C shows representative images of longitudinal expression of the control or Gi-DREADD according to the rostral-caudal axis of the hippocampus of D2-Cre mice.

Figure 10:
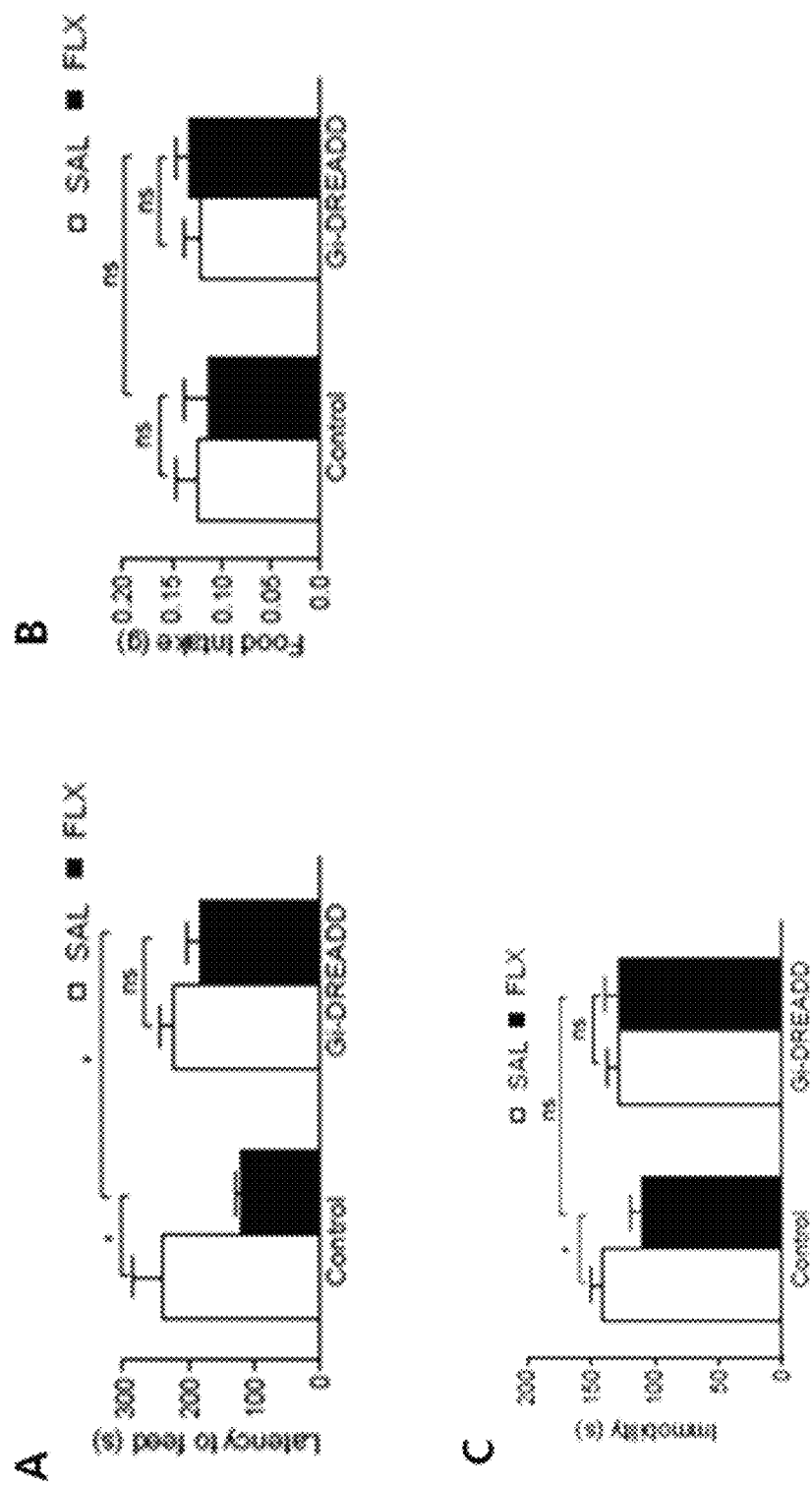

FIG. 10 shows the effect of Gi-DREADD inhibition of mossy cells on behavioral responses to chronic SSRI administration:

FIG. 10A is a result of an NFS test after Gi-DREADD inhibits the activity of mossy cells; FIG. 10B is a result of evaluating hunger levels in the control and Gi-DREADD group through a HCF test; and FIG. 10C is a result of confirming despair or a depression-like behavior pattern in a tail hanging test.

Figure 11:
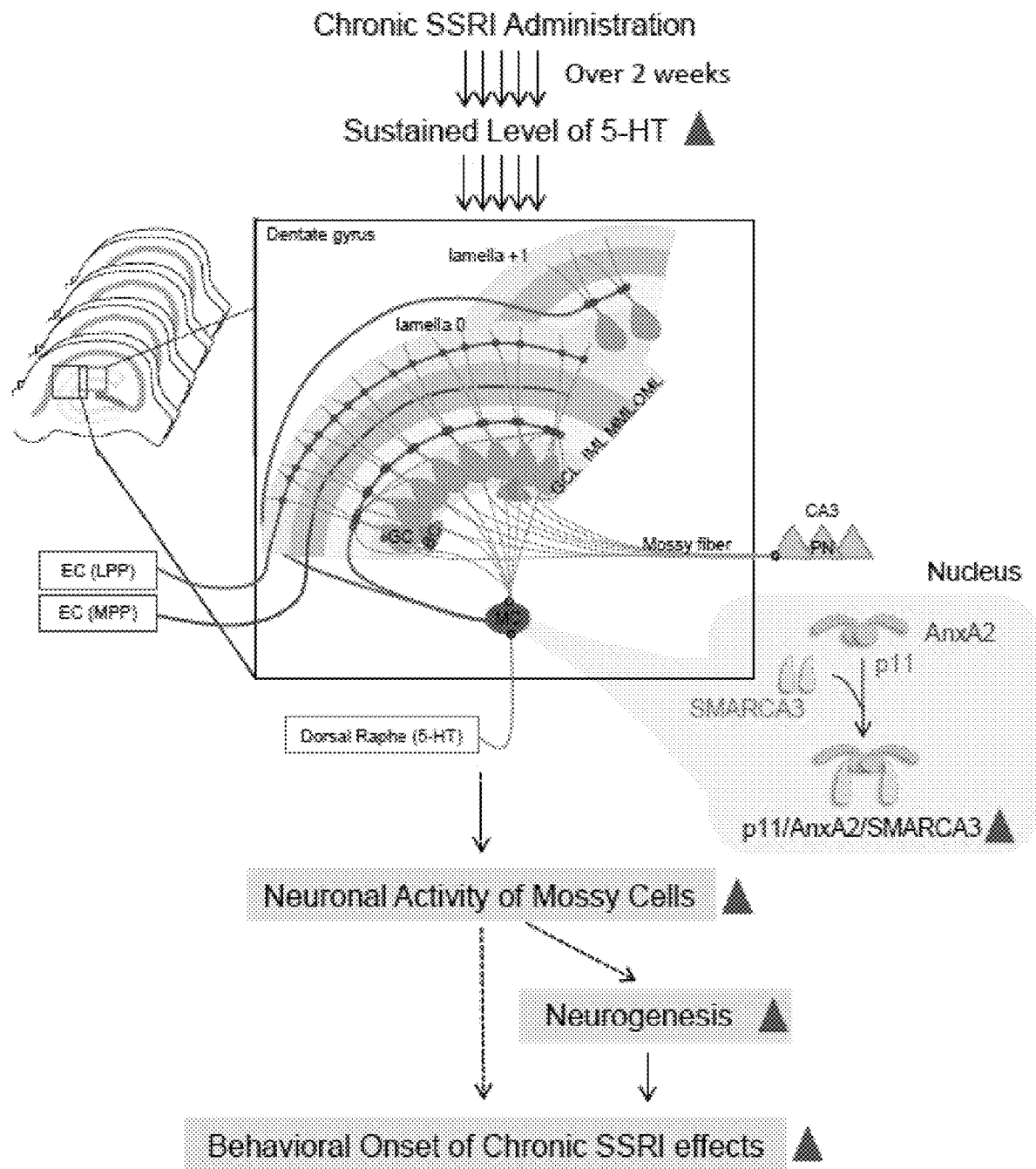

FIG. 11 is a schematic diagram illustrating the effect of the activity change in mossy cells on neurogenic and behavioral responses to chronic SSIR administration.

DETAILED DESCRIPTION

Hereinafter, to help in understanding the present invention, exemplary examples will be suggested. However, the following examples are merely provided to more easily understand the present invention, and not to limit the present invention.

Example 1. Experimental Materials and Preparation 1-1. Animal Breeding

To produce various animal models of the same age, which were sufficient for a behavioral test and other animal tests, the progeny of each line was produced using in vitro fertilization (IVF) and an embryo transfer (ET) technique. All animal tests used littermates matched in age (10 to 15 weeks) and sex (male). Hemizygotes were obtained by mating a BAC-[Drd2]-Cre Tg mouse (GENSAT, Clone #ER44) and an MC-Cre ([Calcrl]-Cre mouse (JAX stock #023014) with a C57BL/6 mouse (Taconics). A p11-Flox mouse and an Smarca3-Flox mouse were prepared by introducing a relevant gene into a flanked loxP site as described in a previous study. All experimental animals were bred at room temperature (22±1° C.) with a 2-hour light/dark cycle, fed a standard diet and water ad libitum. For all experiments, male mice were used.

1-2. Drug Treatment

For chronic drug administration, 2 to 5 mice were housed in each cage. Fluoxetine hydrochloride (Spectrum Chemicals, USA) was intraperitoneally injected (10 mg kg-1 day-1) daily for 3 weeks. The drug was prepared by being dissolved in dimethyl sulfoxide (50%), and diluted with saline. For a control, a drug-free vehicle solution (0.9% saline) was administered daily. For a Gi-DREADD mouse experiment, clozapine-N-oxide (CNO; Sigma-Aldrich, USA) was directly dissolved in a 0.9% saline solution. A dose of CNO was 0.3 mg/kg, and 2 hours before each behavioral test, 100 µl/10 g of a solution per body weight was intraperitoneally injected.

1-3. Construction of Plasmid Constructs

A PASIP (p11/AnxA2/SMARCA3 complex inhibitory peptide) sequence was derived from a binding site between AHNAK1 (amino acids 5654-5671) and the p11/AxnA2 complex. Afterward, the inventors designed a series of PASIP constructs as follows: 1) control AcGFP1 (pAAV-Ef1α-DIO-AcGFP1-myc.hGH), 2) PASIP-AcGFP1c (pAAV-Ef1α-DIO-PASIP-AcGFP1-myc.hGH) and 3) nucleus-targeting PASIP-AcGFP1-NLS (pAAV-Efla-DIO-PASIP-AcGFP1-myc-C3xNLS.hGH).

A coding sequence of the PASIP construct was prepared using a standard gene synthesis method (GENEWIZ, USA), and a pAAV-Ef1α-DIO-EYFP vector (Addgene, #29056) was subcloned at a restriction site recognized by two restriction enzymes (NheI, AscI).

1-4. Immunoprecipitation of p11/AnxA2/SMARCA3 Complex

HEK293 cells (CRL-1573, ATCC) were transfected with a CMV-Cre plasmid, and 24 hours after transfection, transfected with an AAV vector expressing the control AcGFP1 or PASIP-AcGFP1 construct. Immunoprecipitation was performed with α-SMARCA3 antibodies (rabbit polyclonal antibodies prepared with immunized peptides). Immunoblotting was performed using the following antibodies according to a standard protocol: α-p11 (mouse monoclonal, 1:1000, BD Biosciences), α-p11 (goat polyclonal, 1:200, R&D Systems), α-SMARCA3 (goat polyclonal, 1:200, NOVUS), α-AnxA2 (mouse monoclonal, Santa Cruz Biotech.), α-GFP (goat polyclonal, Santa Cruz Biotech).

1-5. Stereotaxic Surgery

Stereotaxic injection of AAVs into mice was performed on an Angle Two™ stereotactic frame (Leica, Buffalo Grove, Ill., USA). Before the stereotactic injection of AAVs, the mice were anesthetized by intraperitoneal injection of avertin (100 mg/kg). Cre-dependent AAVs were stereotactically injected bilaterally into the dorsal and ventral regions of the dentate gyrus using a 10 μl Hamilton syringe (33-gauge needle; Reno, Nev., USA) (coordinates for the dorsal area: AP −2.1ML ±1.4DV-1.95, coordinates for the ventral area: AP-3.3ML ±2.7DV-3.6). A flow rate (0.2 μl/min) was adjusted by a nanopump controller (WPI, US). After viral injection, the needle was maintained for 5 minutes, and then an incision was closed. Mice were placed back in the home cage for recovery. All experimental animals took a rest for at least two weeks before the next experimental step.

1-6. Behavioral Test

In all behavioral tests, within 1 hour before the test, target mice were brought to a test site. All tests were performed by testers who were not provided information on treatment or genotype, and the test was performed in a light cycle of the light/dark cycle.

(1) Elevated Plus Maze (EPM)

In this test, as a plus-type maze structure, a maze place 50 cm above the floor, which has two open arms and two enclosed arms (30 cm long and 5 cm wide) was used. Mice were placed in the center of the maze, and allowed to freely move into the four arms for 10 minutes. The behaviors of the mice were videotaped, and the total amount of time spent in the open and closed arms were recorded and measured using Ethovision™ software (Noldus, USA).

(2) Open Field Test (OF)

Mice were placed in the center of an open field area (40×40×40 cm, Plexiglas chamber). The mice were allowed to freely move in the open field for 1 hour. The duration in the center and periphery was measured using an automated Superflex™ software (Accuscan Instruments, Columbus, Ohio, USA). The measurement was automatized using two rows of infrared photocells placed 20 to 50 nm above the floor at an interval of 31 mm. The interruption of a photocell beam was recorded using Superflex™ software.

(3) Light and Dark Box Test (LD Box)

Mice were placed in an open field area (40×40×40 cm). A black box was inserted into the open field. The mice were placed into light compartments at the beginning of a session, and allowed to freely move between the compartments for 10 minutes. The time spent in each compartment and the latency to first enter the dark compartment were measured using automated Superflex™ software.

(4) Novelty Suppressed Feeding Test (NSF)

The test was carried out for 15 minutes by partially changing a conventional method. 24 hours before behavioral testing, all food provided to the home cage was removed. At the end of the experiment, a single 1.8-cm square-shaped food pellet was placed on a white filter paper positioned in the center of the test box. The mouse was placed in the corner of an open field, and a stopwatch was immediately operated. The latency to first bite food was recorded. Immediately after the test, the mice were placed in the home cage, and the amount of food intake was measured for 10 minutes.

(5) Tail Suspension Test (TST)

Mice were suspended by tails for 6 minutes. A test session was videotaped, and their immobility was scored using automated TST analysis software of Clever System (Reston, Va., USA). The immobility time during the last 4 minutes (excluding the initial 2 minutes) was calculated.

1-7. Immunohistochemistry

Immunostaining was carried out using the standard free-floating method. Sections were washed three times with PBS for 10 minutes each time, and incubated with 2% normal donkey serum, 0.2% bovine serum albumin and 0.3% Triton-X100. After blocking, the sections were incubated with primary antibodies diluted with a blocking buffer overnight at 4° C., the following primary antibodies were used: α-doublecortin (goat polyclonal, 1:200, Santa Cruz Biotech.), α-calretinin (mouse monoclonal, 1:500, SWANT), α-parvalbumin (rabbit polyclonal, 1:1000, SWANT), α-neuropeptide Y (rabbit polyclonal, 1:1000, Phoenix Pharmaceutical), α-GluR2/3 (rabbit polyclonal, 1:100, Millipore). After incubation for 24 hours, the sections were washed three times with PBS containing 0.2% Triton-X100 (PBS-T) for 10 minutes, and then incubated with Alexa-Fluor™-conjugated secondary antibodies (1:400, Life Technologies, USA) at room temperature for 3 hours. The sections were washed three times with PBS-T at room temperature for 10 minutes, and covered with a Prolong™ Gold, anti-fading mounting medium (Life Technologies, USA).

1-8. BrdU Labeling and Neurogenic Analysis

Before the mice were sacrificed, a BrdU solution (200 mg/kg) was intraperitoneally administered for 3 hours. After transcardial perfusion, brain tissue was fixed with 4% PFA overnight, coronal sections with a 40-μm thickness were collected along the hippocampal rostro-caudal axis using a cryostat (CM3050S, Leica). The sections were processed using a free-floating method. Every sixth section throughout the hippocampus was subjected to BrdU immunohistochemical staining. Afterward, sections were pre-incubated with 1M HCl at 45° C. for 30 minutes to denature DNA, and washed three times with 0.1M PBS for neutralization. Immunohistochemistry was performed with α-BrdU (rat polyclonal, 1:200, Abcam, Cambridge, Mass., USA) and Alexa-Fluor™-conjugated secondary antibodies (1:400, Life Technologies, USA). A tester who was not given information on a slide code counted BrdU-labeled cells in the granule cell layer (GCL) and the subgranular zone (SGZ) of the dentate gyrus (DG) in the total of 12 sections derived from individual mice. The total number of BrdU-labeled cells per section was determined and multiplied by 6 to obtain the total number of cells per dentate gyrus.

1-9. Electrophysiological Evaluation of Hippocampal Mossy Cells (1) Fluorescence Labeling of Mossy Cells To label and visualize mossy cells in hippocampal slices, a recombinant AAV vector (AAV2.EF1α.DIO.AcGFP1-myc) was bilaterally injected into the dentate hilus of the ventral hippocampus in MC-Cre ([Calcrl]-Cre) Tg mice. AcGFP1 was selectively expressed in the mossy cells. While recording the electrophysiological evaluation, the morphology, membrane capacitance and electrophysiological properties of the mossy cells were further confirmed.

(2) Preparation of Slices 12-15-week male mice were euthanized with $CO_2$. Subsequently, their brains were extracted and placed in an N-Methyl-D-glucamine-containing cutting solution (93 mM NMDG, 2.5 mM KCl, 1.2 mM $NaH_2PO_4$, 30 mM $NaHCO_3$, 25 mM glucose, 20 mM HEPES, 5 mM sodium ascorbate, 3 mM sodium pyruvate, 2 mM thiourea, 0.5 mM CaCl$_2$), 10 mM MgSO$_4$. pH 7.4, 295-305 mM mOsm) on cold ice. The brain tissue slices (400-µm thickness) containing the ventral hippocampus were prepared using a VT1000 S Vibratome (Leica Microsystems Inc., Buffalo Grove, Ill., USA). After cutting, slices were allowed to recover in the cutting solution at 37° C. for 15 minutes, and then transferred to a recording solution at room temperature for at least 1 hour before recording of the electrophysiological evaluation.

(3) Electrophysiological Recording

Electrophysiological recordings were performed as described above. During recording, brain slices were placed in a perfusion chamber attached to a fixed stage of an upright microscope BX51WI (Olympus, Tokyo, Japan), and immersed in a continuously flowing oxygenated recording solution. Components contained in the solution are as follows: 125 mM NaCl, 25 mM NaHCO$_3$, 25 mM glucose, 2.5 mM KCl, 1.25 mM NaH$_2$PO$_4$, 2 mM CaCl$_2$) and 1 mM MgCl$_2$, pH 7.4, 295-305 mM mOsm. Neurons were visualized with a 40× water immersion lens using near infrared (IR) light. Electrophysiological recording was performed using a Multiclamp 700B/Digidata 1440A system (Molecular Devices, Sunnyvale, Calif., USA). Patch electrodes were filled with an internal solution (126 mM K-gluconate, 10 mM KCl, 10 mM HEPES, 10 mM phosphocreatine, 4 mM ATP and 0.3 mM GTP, pH 7.3, 290 mM mOsmol). Whole-cell patch-clamp recordings were used to record spontaneous action potentials of mossy cells in the hippocampal slices, and all recording was performed at 37° C. In the chemogenic experiment, action potentials of mossy cells were recorded for 5 minutes according to the criteria. In addition, CNO (1 mM) was perfused on the brain tissue slices to confirm the effect of Gi-DREADD. Experimental data was analyzed by pClamp10 software (Molecular Devices) and GraphPad Prism 6 (GraphPad Software, La Jolla, Calif., USA).

1-10. Statistical Analysis

All experimental data was expressed as means±standard deviation. Statistical analysis was performed using GraphPad Prism Version 7.0a. Comparison between two groups was performed by a two-tailed, unpaired Student's t test. The comparison between multiple groups was evaluated using a one-way or two-way ANOVA, followed by a post hoc Bonferroni test. Significant levels are as follows: *p<0.05, p<0.01, *p<0.001.

Figure 1:
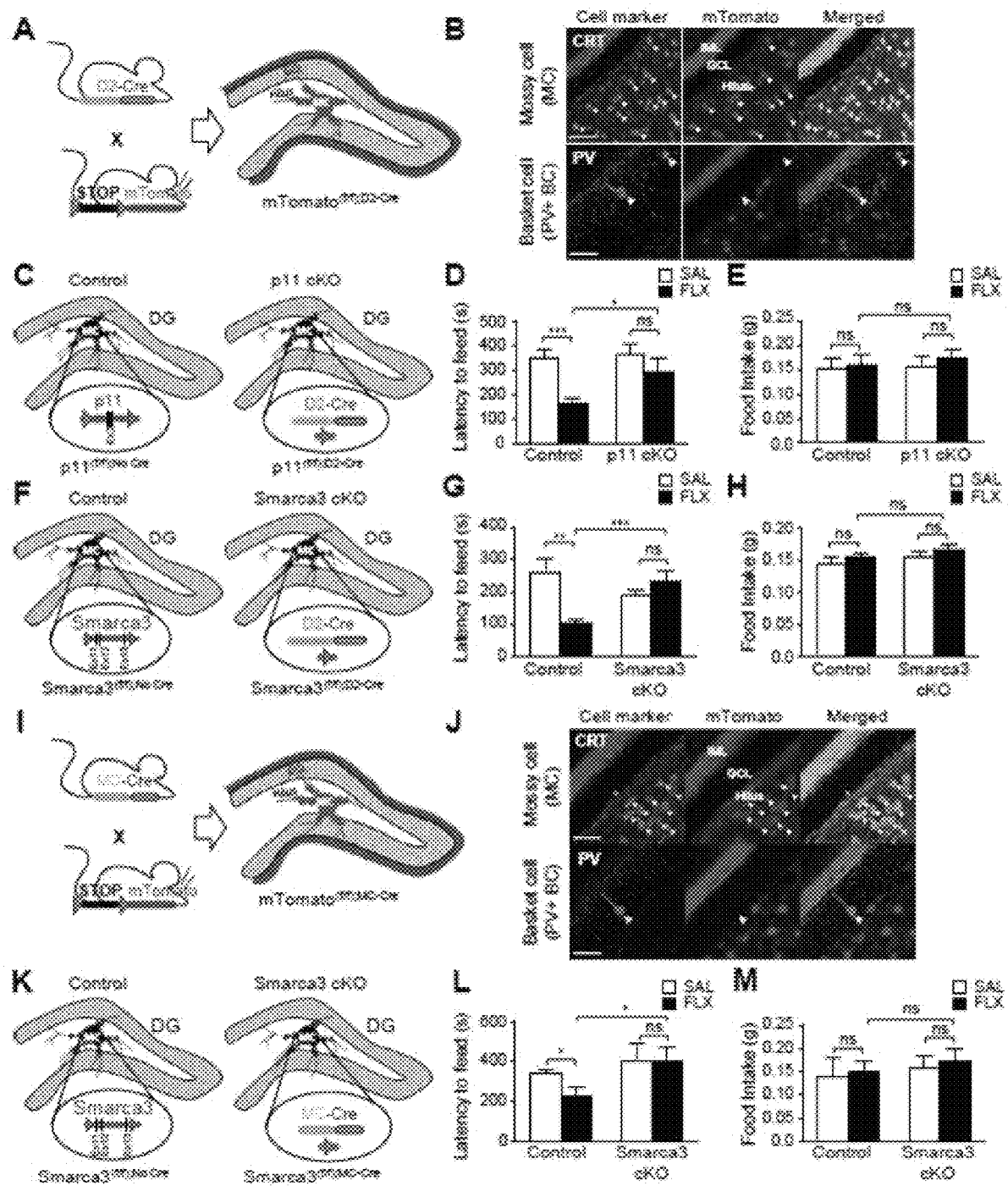
FIG. 1 shows the effect of the genetic deletion of p11 or Smarca3 in hippocampal mossy cells on behavioral responses to chronic administration of SSRI.

Example 2. Effect of Genetic Deletion of p11 or Smarca3 in Hippocampal Mossy Cells on Behavioral Responses to Chronic SSRI Administration In the embodiment, the specific relevance of the p11/AnxA2/SMARCA3 complex to an antidepressant action was confirmed. First, the inventors specifically confirmed the role of a ternary complex in a specific cell type by preparing conditional KO mice with mossy cell-specific deletion of p11 or Smarca3. To investigate mossy cell-specific functionality of p11 and/or Smarca3 in terms of antidepressant actions, hippocampal mossy cells were targeted using a transgenic Cre driver line. That is, the expression of dopamine D2 receptor promoter-driven Cre recombinase in a mossy cell-specific manner in the dentate gyrus was validated by crossing a D2-Cre ([Drd2]-Cre) driver mouse line including a mossy cell-specific dopamine D2 receptor promoter and Cre recombinase with an mTomato reporter line (see FIGS. 1A and 1B). Afterward, specific deletion of p11 or Smarca3 in mossy cells was induced by crossing with a p11 or Smarca3 flox conditional line (see FIGS. 1C and 1F). After SSRI was chronically administered to the p11 or Smarca3 conditional KO (cKO) line, an NFS test was performed to investigate a depression-like state. As a result, in a control in which a relevant gene was not knocked out, as an effect caused by the SSRI administration, the latency to access a food pellet was reduced (p11$^{(f/f)}$: SAL vs FLX, 351±38 vs 165±24, p<0.001; and Smarca3$^{(f/f)}$: SAL vs FLX, 257±47 vs 104±12, p<0.01).

However, these reduction effects were not observed in p11 conditional knockout mice (p11$^{(f/f);D2-Cre}$: SAL vs FLX, 364±46 vs 296±58; p=0.37), or Smarca3 conditional knockout mice (Smarca3$^{(f/f);D2-Cre}$: SAL vs FLX, 192±15 vs 232±32, p=0.24) (see FIGS. 1D and 1G). In addition, after coming back to the home cage, it was confirmed that there was no change in food intake (see FIGS. 1E and 1H).

In addition, these effects caused by genetic deletion of SMARCA3 in mossy cells were additionally validated using another type of mossy cell-specific Cre mouse line, MC-Cre ([Calcrl]-Cre). The MC-Cre line is very specific to the hippocampus, but exhibited wide activity in both mossy cells present near the hilus of the dentate gyrus and pyramidal cells of a CA3 region. The inventors deleted the Smarca3 gene by crossing MC-Cre mice with Smar3 flox conditional mice (Smarca3$^{(f/f)}$) (see FIG. 1K), an NSF test was performed after chronic administration of SSRI. As a result, in a control in which a relevant gene was not knocked out, as an effect caused by SSRI administration, the latency to access a food pellet was reduced (Smarca3$^{(f/f)}$: SAL vs FLX, 338±20 vs 229±40; p<0.05). However, in Smarca3 conditional knockout mice (Smarca3$^{(f/f);MC-Cre}$: SAL vs FLX, 405±88 vs 404±69, p=0.99, or Smarca3$^{(f/f);D2-Cre}$: SAL vs FLX, 192±15 vs 232±32, p=0.24), such a reduction effect was not observed either (see FIGS. 1L and 1M).

Such experimental results show that selective deletion of p11 or Smarca3 in mossy cells of the dentate gyrus affects an antidepressant response. That is, it shows that p11 and Smarca3 in the mossy cells are directly involved in behavioral responses to chronic antidepressant treatment.

Example 3. Effect of Cell-Specific Inhibition of p11/AnxA2/SMARCA3 Complex on Neurogenic and Behavioral Responses to Chronic SSRI Administration In Example 2, the effect of the genetic deletion of p11 or Smarca3 on antidepressant responses was specifically confirmed using mossy cell-specific KO mice, and such a transgenic approach cannot rule out whether the above-described effect is a behavioral change caused by developmental defects or off-target deletion of the p11 or Smarca3 gene in cKO mice. Therefore, the inventors further investigated neurogenic and behavioral effects of mossy cell-specific inhibition of the p11/AnxA2/SMARCA3 complex in adult mice. To this end, first, recombinant constructs that inhibit the assembly of the p11/AnxA2/SMARCA3 complex were obtained. The p11/AnxA2 heterotetramer was shown to form a stable heterohexamer with SMARCA3 or AHNAK1 according to very similar recognition principles (not shown). In addition, a short peptide derived from a SMARCA3 or AHNAK1 binding site forms a stable complex with the p11/AnxA2 heterotetramer by being placed in a hydrophobic binding pocket formed on the surface of the p11/AnxA2 heterotetramer complex. Accordingly, based on information on the co-crystallization structure of the ternary complex, a recombinant inhibitor of the p11/AnxA2/

Figure 2:
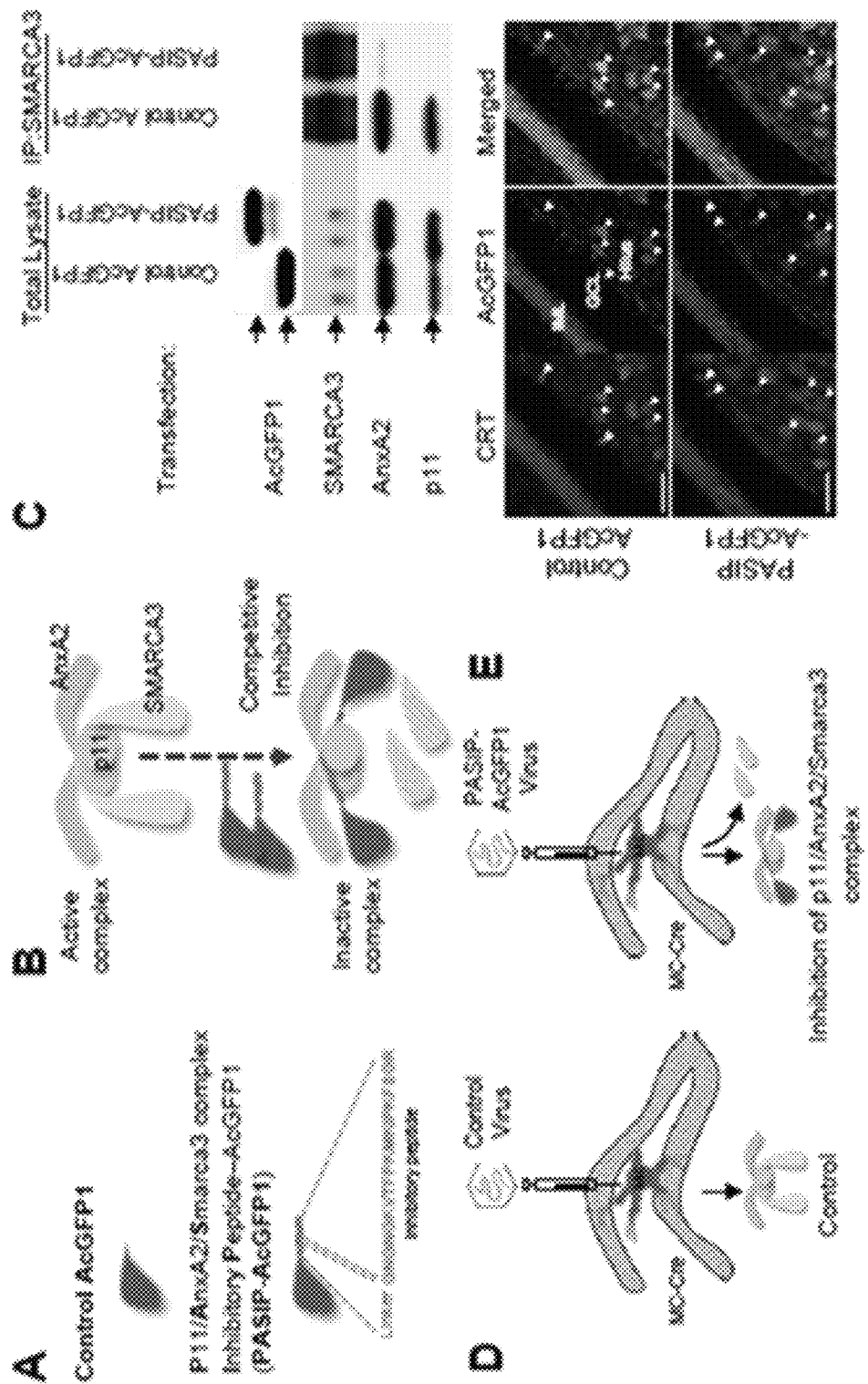
FIG. 2 shows the effect of mossy cell-specific disruption of a p11/AnxA2/SMARCA3 complex on neurogenic and behavioral responses to chronic treatment of SSRI.

SMARCA3 complex (p11/AnxA2/SMARCA3 complex inhibitory peptide-AcGFP1 fusion construct; PASIP-AcGFP) was prepared along with an inert control (control AcGFP1) (see FIG. 2A). The inventors assumed that such a recombinant inhibitory construct is present competitively with endogenous SMARCA3 on the binding pocket, and thus blocks the functional assembly of the activated ternary complex, p11/AnxA2/SMARCA3 heterohexamer (see FIG. 2B). In practice, as a result of an in vitro immunoprecipitation assay, it was confirmed that the recombinant PASIP-AcGFP1 construct is able to block the assembly of the p11/AnxA2/SMARCA3 complex (see FIG. 2C).

Figure 3:
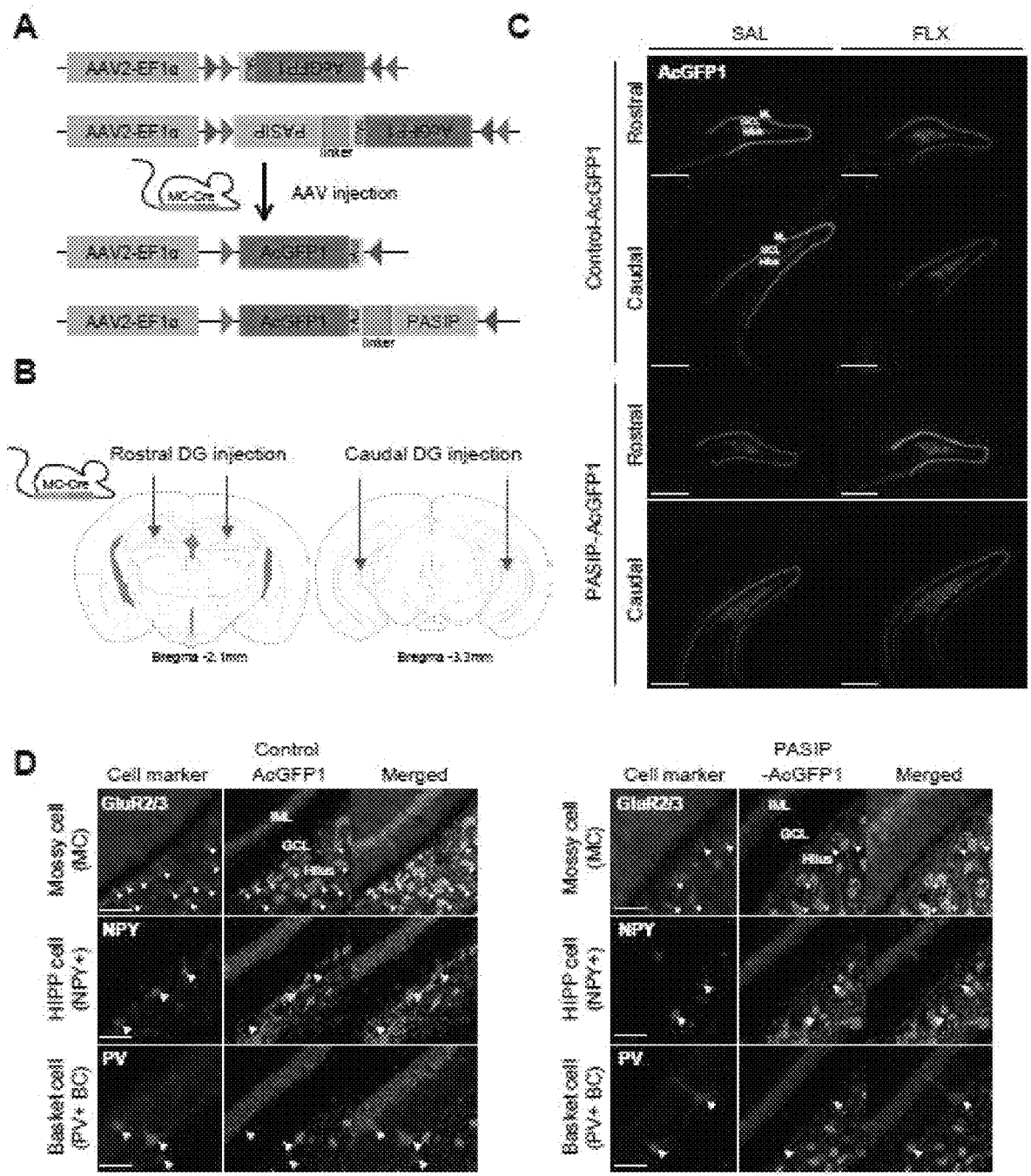
FIG. 3 shows mossy cell-specific expression of the control AcGFP or PASIP-AcGFP1 construct along the rostro-caudal axis of the hippocampus.

In addition, to deliver the PASIP-AcGFP1 construct to hippocampal mossy cells, Cre-dependent AAVs were prepared. The Cre-dependent AAVs were locally injected into rostral and caudal hilus regions of MC-Cre transgenic mice (see FIGS. 2D, 3A and 3B). Since MC-Cre mice display Cre-recombinant constructs in both dentate mossy cells and some pyramidal subpopulations in the CA3 region, a recombinant AAV solution was delivered in the middle of the hilus region to prevent unnecessary diffusion of viral particles. In histological analysis, an AcGFP1 signal was only found in the hilus and an inner molecular layer (IML) which are localized in somas and axonal fibers of mossy cells, and was not found in the CA3 region in which pyramidal cells are present (see FIG. 3C). That is, such a result shows hippocampal site-specific delivery. In addition, AcGFP1-fusion proteins (control AcGFP1 and PASIP-AcGFP1) were specifically expressed in mossy cells, but not in other GABAergic interneurons including PV+ basket cells and NPY+ HIPP cells (see FIGS. 2E and 3D), indicating cell-specific expression in the dentate gyrus.

Figure 4:
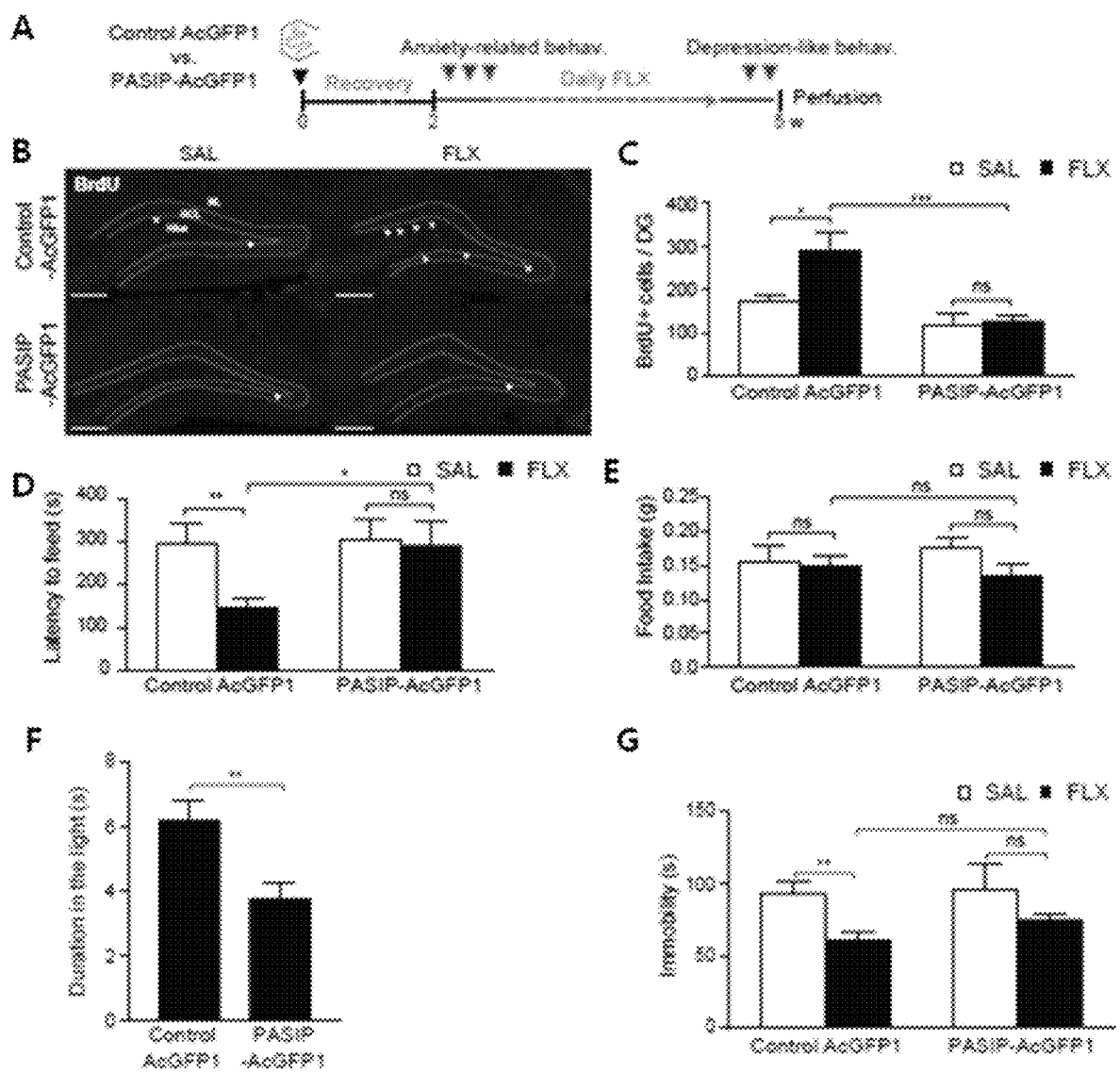
FIG. 4 shows the effect of mossy cell-specific inhibition of the p11/AnxA2/SMARCA3 complex on basal mobility and anxiety-related behavior.

After the formation of p11/AnxA2/SMARCA3 was prevented through mossy cell-specific expression of the PASIP-AcGFP1 construct, the inventors investigated neurogenic and behavioral changes according to chronic administration of SSRI (see FIG. 4A). It is known that adult neurogenesis in the dentate gyrus is induced in response to chronic antidepressant treatment. Therefore, in the control and the PASIP-AcGFP1 mice, the proliferation activity of neural progenitors, which is induced by chronically administered fluoxetine, was evaluated. A significant increase in BrdU+ proliferating cells was observed in control mice chronically treated with fluoxetine (SAL vs FLX, 173±16 vs 290±43; p<0.05), and this effect was not observed in PASIP-AcGFP1 mice (SAL vs FLX, 119±27 vs 129±13; p=0.73) (see FIGS. 4B and 4C).

In addition, the inventors investigated the functional role of the p11/AnxA2/SMARCA3 complex in mossy cells, related to behavioral changes induced by SSRI administration. After chronic administration of fluoxetine, the latency to feed was reduced in control AcGFP1 mice (SAL vs FLX, 296±48 vs 147±22; p<0.01), but not in the PASIP-AcGFP1 mice (SAL vs FLX, 304±51 vs 293±54; p=0.88) (see FIG. 4D). Both fluoxetine treatment or the inhibition of the p11/AnxA2/SMARCA3 complex did not have a significant influence on a home cage feeding level, indicating that such behavioral changes are not caused by the difference in different hunger levels between comparative groups (see FIG. 4E).

In addition, the control AcGFP1 mice and PASIP-AcGFP1 showed a significant difference in light/dark box tests (Control AcGFP1 vs PASIP-AcGFP1, 154±16 vs 94±13; p<0.01) (see FIG. 4F), and like behavioral changes induced by an antidepressant, observed in the NSF test, the inhibition of the p11/AnxA2/SMARCA3 complex reduced an effect caused by fluoxetine administration even in a tail-suspension test (TST) (see FIG. 4G).

In summary, the above results show that the p11/AnxA2/SMARCA3 complex formed in mossy cells plays a critical role in behavioral changes after chronic treatment of SSRIs.

Figure 5:
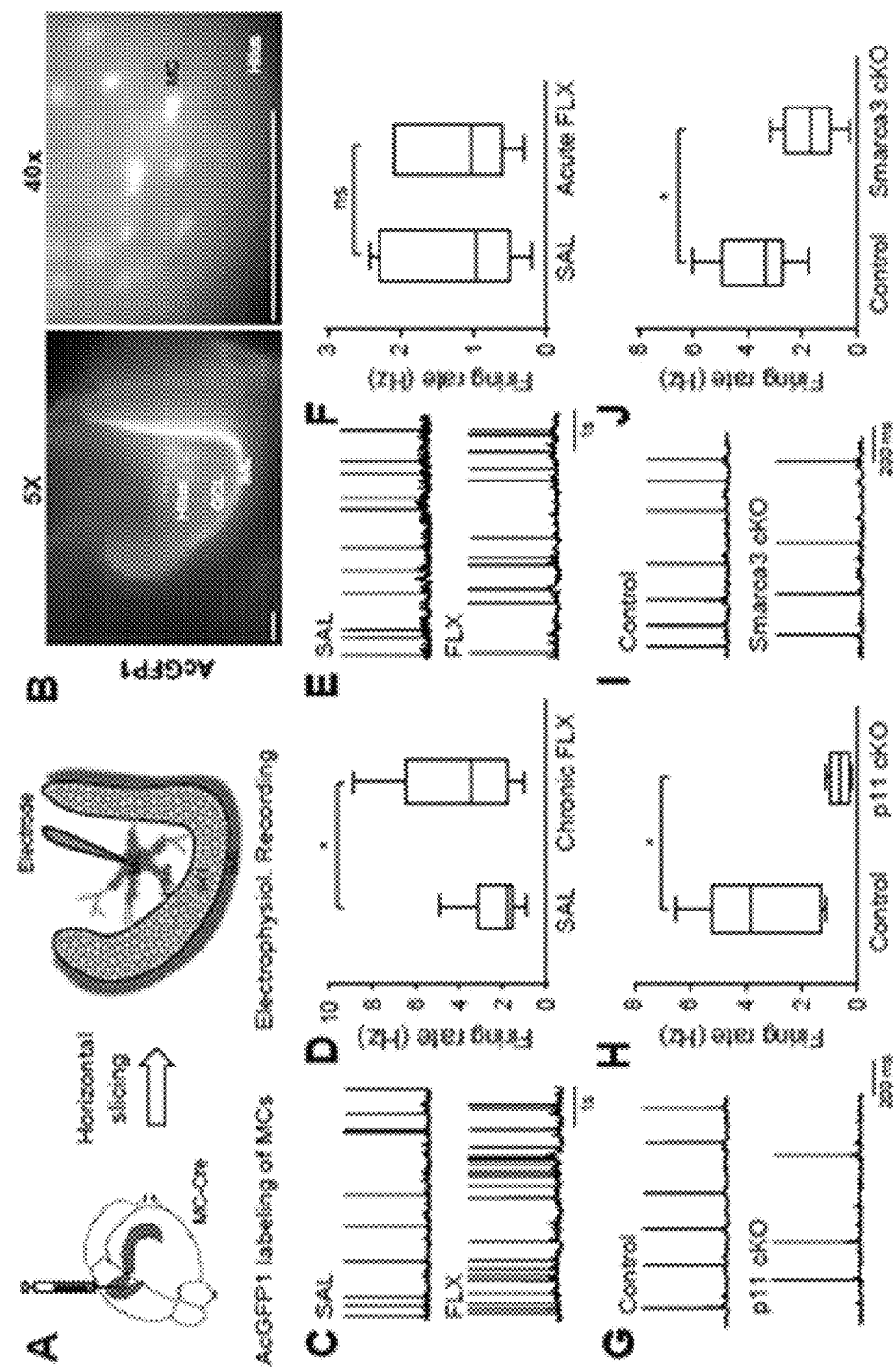
FIG. 5 shows the effect of the p11/AnxA2/SMAR complex on excitability of mossy cells in the dentate gyrus.

Example 4. Effect of Cell-Specific Inhibition of p11/AnxA2/SMARCA3 Complex on Neuronal Activity of Mossy Cells In this example, the effect of the administration of an antidepressant on the neuronal activity of mossy cells was investigated. Mossy cells are neurons that spontaneously control neuronal excitation in the hilus region, and their activity controls neural circuits and functions of the dentate gyrus. For electrophysiological recording of mossy cells, Cre-dependent AcGFP1 AAVs were injected into mossy cell-specific Cre (MC-Cre) mice, and mossy cells were labeled with a fluorescent protein AcGFP1 (see FIG. 5A). As a result, it was able to be confirmed that AcGFP1 is limitedly expressed in mossy cells in the dentate gyrus (see FIG. 5B). In addition, changes in the morphology, tonic firing pattern and membrane capacity (50-100 pF) of the mossy cells were further confirmed. Electrophysiological recordings showed that chronic fluoxetine treatment significantly improved a spontaneous firing rate of mossy cells (control: 2.36±0.41 Hz, fluoxetine: 4.19±0.92 Hz) (FIGS. 5C and 5D), but acute treatment of the drug had no effect on mossy cell activity (control: * Hz, Fluoxetine:  Hz) (see FIGS. 5E and 5F).

In addition, it was confirmed whether p11 and SMARCA3 control mossy cell activity by measuring spontaneous action potential frequency in mossy cells. As a result, it could be confirmed that the spontaneous firing rate of the mossy cells is significantly reduced in p11cKO mice (control: 3.37±0.63 Hz, p11cKO: 0.65±0.10 Hz) (FIGS. 3G and 3H), and resting membrane potentials of the mossy cells were also hyperpolarized in p11 cKO mice (control: −47.70±2.11 mV, p11cKO: −56.01±0.63 mV). As described above, the spontaneous firing rate of the mossy cells was reduced significantly in Smarca3 cKO mice (control: 3.67±0.48 Hz, Smarca3 cKO: 1.75±0.33 Hz) (see FIGS. 5I and 5J). Such experimental results suggest that p11 and SMARCA3 play critical roles in control of neuronal activity of the mossy cells.

Moreover, it was further investigated whether cell-specific inhibition of the p11/AnxA2/SMARCA3 complex caused by the expression of the PASIP-AcGFP1 construct affects the neuronal activity of mossy cells. According to previous research, to control gene transcription, the p11/AnxA2/SMARCA3 complex targeted the nuclear matrix. Therefore, a PASIP-AcGFP1-NLS construct that was specifically targeted to the nucleus of mossy cells through an additional nuclear localization signal (NLS) was prepared (see FIG. 6A). Cre-dependent viral vectors including control AcGFP1, PASIP-AcGFP1 and PASIP-AcGFP1-NLS were prepared (see FIG. 6B). Afterward, cell-type specific expression of the PASIP-AcGFP1-NLS construct and nucleus-specific expression of the PASIP-AcGFP1 construct were verified by co-transfection into cultured HEK cells or stereotactic injection into mossy cell-specific Cre (MC-Cre) transgenic mice (see FIGS. 7A and 7B). In addition, the firing rate of mossy cells was significantly reduced by PASIP-AcGFP1 or PASIP-AcGFP1-NLS expression, compared with control AcGFP1 (control: 3.58±0.56 Hz, PASIP-AcGFP1: 0.64±0.10 Hz, PASIP-AcGFP1-NLS: 1.39±0.36 Hz) (see FIGS. 7C and 7D), and likewise, the resting membrane potential in mossy cells was more hyperpolarized by PASIP-AcGFP1 or PASIP-AcGFP1-NLS (control: −47.33±1.77 mV, PASIP-AcGFP1: −54.33±1.32 mV, PASIP-AcGFP1-NLS: −56.30±1.20 mV).

Collectively, it is demonstrated that the p11/AnxA2/SMARCA3 complex contributes to the control of the activity of mossy cells, and therefore, the changed activity of the mossy cells affects the reactivity or action of an antidepressant.

Example 5. Effect of Selective Inhibition of Mossy Cells on Antidepressant Actions in Hippocampus In the embodiment, it was investigated whether the selective inhibition of mossy cells affects neurogenic and behavioral effects of chronic antidepressant treatment. To control the activity of mossy cells, the inventors applied a Designer Receptors Exclusively Activated by Designer Drug (DREADD) technique. To introduce a Gi-DREADD system into mossy cells, a viral vector expressing control mCherry or hM4D-Gi-mCherry (Gi-DREADD) was injected into rostral and caudal hilus regions of D2-Cre transgenic mice (see FIGS. 8A, 9A and 9B). Afterward, longitudinal expression of the control or Gi-DREADD along the rostral-caudal axis of the hippocampus in the D2-Cre mice was confirmed (see FIG. 9C). In addition, by using electrophysiological recordings of mCherry-labeled mossy cells, it was confirmed that the activity of mossy cells was silenced by the treatment of an artificial agonist of a DREADD system and clozapine N-oxide (CNO), and such an effect was observed only in Gi-DREADD mice, not in control mice (see FIGS. 8C and 8D).

By using the Gi-DREADD system, the inventors investigated the role of mossy cells in neurogenic and behavioral changes induced by chronic fluoxetine administration (see FIG. 8E). Through the BrdU labeling and histological analysis of the control and Gi-DREADD mice, adult neurogenic activity was measured. Chronic SSRI administration significantly increased the number of BrdU+ proliferating cells in the subgranular zone of the dentate gyrus in the control mice (SAL vs FLX, 177±18 vs 337±37; p<0.01), but such an effect caused by fluoxetine treatment disappeared in the Gi-DREADD mice (SAL vs FLX, 172±27 vs 232±20; p=0.89) (see FIGS. 8F and 8G). In addition, as a marker for an immature neuron indicating a snapshot of newborn postmitotic cells in neuronal maturation and differentiation, the expression level of doublecortin (DCX) was analyzed. Chronic fluoxetine administration enhanced the survival of newborn neuronal progenitors and promoted differentiation into mature neurons, but when the activity of mossy cells was inhibited, the survival and/or differentiation of newborn postmitotic cells significantly decreased (see FIGS. 8H and 8I). That is, this experimental result shows a similar tendency to the effect of the inhibition of the p11/AnxA2/SMARCA3 complex of Example 2, and it can be seen that the activity of mossy cells is directly involved in the control of proliferation of neuronal progenitors and differentiation and maturation into newborn granular cells, induced by fluoxetine administration.

Moreover, an influence of mossy cell activity on antidepressant actions was investigated by monitoring general locomotor activity and emotional behavior changes through various behavioral tests. As a result of a novelty-suppressed feeding (NSF) test, behavioral changes induced by chronic administration of an antidepressant were influenced by the inhibition of mossy cell activity induced by CNO, indicating that the effect caused by fluoxetine is counteracted in the Gi-DREADD mice (control: SAL vs FLX, 484±85 vs 238±40; p<0.05, Gi-DREADD: SAL vs FLX, 450±36 vs 365±40; p=14) (see FIG. 10A). In addition, since a home cage feeding level was not influenced by the introduction of the Gi-DREADD system, it was seen that this behavioral change is not caused by a difference in hunger levels between comparative groups (see FIG. 10B). In addition, in the TST, the fluoxetine effect on inactivity significantly decreased in control mice (SAL vs. FLX, 141±9 vs 110±9; p<0.05), but likewise, this effect was not observed in the Gi-DREADD mice (SAL vs FLX, 128±9 vs 129±10, p=0.94) (see FIG. 10C). Collectively, it can be seen that the mossy cell activity in the dentate gyrus plays a critical role in the actions and/or responses of the antidepressant.

The scope of the present invention is represented by the following claims, and all changes or modifications derived from the meaning and scope of the claims and their equivalent concepts should be interpreted as being included in the scope of the present invention.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A peptide for controlling reactivity to a serotonin reuptake inhibitor-based antidepressant, consisting of the amino acid sequence of SEQ ID NO: 1.

2. The peptide of claim 1, wherein the peptide further comprises a nuclear localization sequence (NLS).

3. The peptide of claim 2, wherein the NLS consists of the amino acid sequence of SEQ ID NO: 2.

4. The peptide of claim 1, wherein the peptide inhibits the formation of a p11/AnxA2/SMARCA3 complex in mossy cells.

5. The peptide of claim 4, wherein the peptide inhibits binding between a p11/AnxA2 complex and SMARCA3.

6. The peptide of claim 1, wherein the serotonin reuptake inhibitor-based antidepressant is selected from the group consisting of fluoxetine, citalopram, dapoxetine, escitalopram, fluvoxamine, paroxetine, sertraline, or a combination thereof.

7. A vector comprising a peptide consisting of the amino add sequence of SEQ ID NO: 1.

8. The vector of claim 7, wherein the peptide further comprises a nuclear localization sequence (NLS).

9. The vector of claim 8, wherein the NLS consists of the amino acid sequence of SEQ ID NO: 2.

10. The vector of claim 7, wherein the vector is selected from the group consisting of a plasmid, an adenovirus, an adeno-related virus, a retrovirus, a lentivirus, a herpes simplex virus and a vaccinia virus.

11. A method of treating depression, comprising:
administering to a subject in need thereof an effective amount of the peptide of claim 1.

12. The method of claim 11, wherein the peptide inhibits the activity of p11 in the lateral habenula.

13. The method of claim 11, wherein the peptide is co-administered with a serotonin reuptake inhibitor.

14. The method of claim 11, wherein the peptide further comprises a nuclear localization sequence (NLS).

15. The method of claim 14, wherein the NLS consists of the amino acid sequence of SEQ ID NO: 2.

16. A method of controlling reactivity to a serotonin reuptake inhibitor-based antidepressant, comprising:
administering to a subject in need thereof an effective amount of a peptide consisting of the amino acid sequence of SEQ ID NO: 1.

17. The method of claim 16, wherein the peptide further comprises a nuclear localization sequence (NLS).

18. The method of claim 17, wherein the NLS consists of the amino acid sequence of SEQ ID NO: 2.

* * * * *